US011268113B2

(12) United States Patent
Aoki et al.

(10) Patent No.: US 11,268,113 B2
(45) Date of Patent: Mar. 8, 2022

(54) PHA-PRODUCING MICROORGANISM IN WHICH GLYCEROL KINASE ACTIVITY IS ENHANCED, AND PHA PRODUCTION METHOD USING SAME

(71) Applicant: KANEKA CORPORATION, Osaka (JP)

(72) Inventors: Rina Aoki, Takasago (JP); Shunsuke Sato, Takasago (JP)

(73) Assignee: KANEKA CORPORATION, Osaka (JP)

(*) Notice: Subject to any disclaimer, the term of this patent is extended or adjusted under 35 U.S.C. 154(b) by 41 days.

(21) Appl. No.: 16/616,276

(22) PCT Filed: May 23, 2018

(86) PCT No.: PCT/JP2018/019815
§ 371 (c)(1),
(2) Date: Nov. 22, 2019

(87) PCT Pub. No.: WO2018/216726
PCT Pub. Date: Nov. 29, 2018

(65) Prior Publication Data
US 2020/0087687 A1 Mar. 19, 2020

(30) Foreign Application Priority Data
May 25, 2017 (JP) ............................ JP2017-103343

(51) Int. Cl.

| | |
|---|---|
| ***C12N 1/20*** | (2006.01) |
| ***C12P 7/62*** | (2006.01) |
| ***C12N 9/10*** | (2006.01) |
| ***C12N 15/74*** | (2006.01) |
| ***C12P 7/625*** | (2022.01) |

(52) U.S. Cl.
CPC .................. *C12P 7/62* (2013.01); *C12N 1/20* (2013.01); *C12N 9/1029* (2013.01); *C12N 15/74* (2013.01); *C12P 7/625* (2013.01)

(58) Field of Classification Search
None
See application file for complete search history.

(56) References Cited

U.S. PATENT DOCUMENTS

2012/0135480 A1 5/2012 Nakas et al.
2017/0198313 A1 7/2017 Kobayashi et al.
2020/0087687 A1* 3/2020 Aoki ......................... C12P 7/62

FOREIGN PATENT DOCUMENTS

WO WO 2004/065253 A2 8/2004
WO WO 2015/146195 A1 10/2015

OTHER PUBLICATIONS

GenBank Accession No. AQV94885.1, published Mar. 3, 2017 (Year: 2017).*
International Search Report dated Aug. 28, 2018 in PCT/JP2018/019815 filed on May 23, 2018, 2 pages.
Fukui et al., "Enhancement of glycerol utilization ability of *Ralstonia eutropha* H16 for production of polyhydroxyalkanoates", Appl. Microbiol. Biotechnol., 2014, vol. 98, pp. 7559-7568.
Extended European Search Report dated Feb. 26, 2021 in European Patent Application No. 18806141.0.
S. Povolo, et al., "Poly(hydroxyalkanoate) Production by *Cupriavidus necator* from Fatty Waste Can Be Enhanced by phaZ1 Inactivation," Chemical and Biochemical Engineering Quarterly, vol. 29, No. 2, XP55776120, 2015, pp. 67-74.

* cited by examiner

*Primary Examiner* — Richard C Ekstrom
(74) *Attorney, Agent, or Firm* — Oblon, McClelland, Maier & Neustadt, L.L.P.

(57) ABSTRACT

Provided are a PHA-producing microorganism producing a higher molecular weight PHA and a PHA production method using the PHA-producing microorganism. A PHA-producing microorganism including a gene encoding a PHA synthase derived from genus *Aeromonas*, in which at least a portion of a PHA degrading enzyme gene is altered by substitution, deletion, insertion, and/or addition to reduce or eliminate activity of a PHA degrading enzyme encoded by the gene, and further a glycerol kinase activity is enhanced.

14 Claims, No Drawings

Specification includes a Sequence Listing.

PHA-PRODUCING MICROORGANISM IN WHICH GLYCEROL KINASE ACTIVITY IS ENHANCED, AND PHA PRODUCTION METHOD USING SAME

TECHNICAL FIELD

The present invention relates to a PHA-producing microorganism in which glycerol kinase activity is enhanced, and a PHA production method using the PHA-producing microorganism.

BACKGROUND ART

Polyhydroxyalkanoates (hereinafter, referred to as "PHAs") are thermoplastic polyesters produced in cells of a variety of microorganisms. PHAs have a biodegradablility and are producible from renewable resources. Hence, some attempts have been made to employ PHA as an environmentally friendly material or biocompatible material for various industrial use.

The constituent component of PHAs is hydroxyalkanoic acid which is specifically exemplified by 3-hydroxypropionic acid, 3-hydroxybutyric acid, 3-hydroxyvaleric acid, 3-hydroxyhexanoic acid, and 3-hydroxyoctanoic acid, and 3-hydroxyalkanoic acids with a longer alkyl chain, and 4-hydroxybutyric acid. These hydroxyalkanoic acids are homopolymerized or copolymerized to form PHA.

Examples of such PHA include poly-3-hydroxybutyric acid (hereinafter sometimes referred to as P(3HB)), which is a homopolymer of 3-hydroxybutyric acid (hereinafter sometimes referred to as 3HB). Examples of such PHA further include a copolymer of 3HB and 3-hydroxyvaleric acid (hereinafter sometimes referred to as 3HV) (the copolymer is hereinafter sometimes referred to as P(3HB-co-3HV)) and a copolymer of 3HB and 3-hydroxyhexanoic acid (hereinafter sometimes referred to as 3HH) (the copolymer is hereinafter sometimes referred to as P(3HB-co-3HH)). Examples of such PHA furthermore include a copolymer of 3HB and 4-hydroxybutyric acid (hereinafter sometimes referred to as 4HB) (the copolymer is hereinafter sometimes referred to as P(3HB-co-4HB)).

PHAs have different physical properties depending on the molecular weight. For example, PHAs with as high a molecular weight as possible are preferred in the case of fiber processing. On the other hand, in refinement steps and processing steps of PHA, the molecular weight is lowered by treatment with heat, acid, alkali or the like. Thus, in order to maintain the molecular weight of PHA in a PHA product so as to be capable of exhibiting desired physical properties, it is essential to develop a PHA molecular weight control technology in a fermentation production process, particularly a technology for further increasing the molecular weight, which plays an important role in industrial use.

As the PHA molecular weight control technology, Patent Literature 1 reports a method of producing a higher molecular weight PHA by disrupting a gene for a PHA degrading enzyme of *Cupriavidus necator* as a PHA-producing microorganism. With this technology, a decrease in the molecular weight of PHA can be prevented by suppressing degradation of PHA produced in the microorganism, and PHA with a higher molecular weight can be obtained.

CITATION LIST

Patent Literature

PTL 1: WO 04/065253

SUMMARY OF INVENTION

Technical Problem

However, from the viewpoint that it is desirable to obtain a higher molecular weight PHA in the fermentation production process, there is still room for improvement in the technology disclosed in Patent Literature 1.

An object of the present invention is to provide a PHA-producing microorganism producing a higher molecular weight PHA and a PHA production method using the PHA-producing microorganism.

Solution to Problem

The present inventors have made intensive studies on breeding a microorganism producing a high molecular weight PHA. As a result, the present inventors have found that enhancement of glycerol kinase activity in a PHA-producing microorganism in which an activity of a PHA degrading enzyme is reduced or eliminated, in particular, in *Cupriavidus necator* allows for production of a high molecular weight PHA. The present invention has been completed based on this finding.

That is, the present invention relates to the following [1] to [13].

[1] A PHA-producing microorganism including a gene encoding a PHA synthase derived from genus *Aeromonas*, in which at least a portion of a PHA degrading enzyme gene is altered by substitution, deletion, insertion, and/or addition to reduce or eliminate activity of a PHA degrading enzyme encoded by the gene, and further a glycerol kinase activity is enhanced.

[2] The PHA-producing microorganism according to [1], in which the gene encoding a PHA synthase is derived from *Aeromonas caviae.*

[3] The PHA-producing microorganism according to [1] or [2], in which the glycerol kinase activity is enhanced by introducing a gene encoding exogenous glycerol kinase.

[4] The PHA-producing microorganism according to [3], in which the gene encoding exogenous glycerol kinase is derived from genus *Escherichia.*

[5] The PHA-producing microorganism according to [4], in which the gene encoding exogenous glycerol kinase is derived from *Escherichia coli.*

[6] The PHA-producing microorganism according to [1] or [2], in which the glycerol kinase activity is enhanced by enhancing an endogenous glycerol kinase activity inherent in a host of the PHA-producing microorganism.

[7] The PHA-producing microorganism according to any one of [1] to [6], in which a glycerol uptake activity into cells is not enhanced.

[8] The PHA-producing microorganism according to any one of [1] to [7], in which the PHA-producing microorganism is a transformant including a microorganism belonging to genus *Cupriavidus* as a host.

[9] The PHA-producing microorganism according to [8], in which the microorganism belonging to genus *Cupriavidus* is *Cupriavidus necator.*

[10] A PHA production method, including a step of culturing the PHA-producing microorganism according to any one of [1] to [9].

[11] The PHA production method according to [10], in which in the culture step, a carbon source containing glycerol and/or a compound containing a glycerol skeleton is used.

[12] The PHA production method according to [10] or [11], in which the PHA is a copolymerized PHA containing a structural unit derived from 3-hydroxybutyric acid.

[13] The PHA production method according to [12], in which the copolymerized PHA contains a structural unit derived from at least 3-hydroxybutyric acid and 3-hydroxyhexanoic acid.

Advantageous Effects of Invention

According to the present invention, a higher molecular weight PHA can be produced.

DESCRIPTION OF EMBODIMENTS

Preferred embodiments of the present invention will be described, but the present invention is not limited to those embodiments.

A first characteristic of the PHA-producing microorganism used in the present invention is that the PHA-producing microorganism has a gene encoding a PHA synthase derived from genus *Aeromonas*. The gene encoding a PHA synthase derived from the genus *Aeromonas* is not particularly limited, but the gene is preferably a gene encoding a PHA synthase capable of synthesizing a copolymerized PHA containing at least 3HB as a monomer unit, more preferably a gene encoding a PHA synthase capable of synthesizing a copolymerized PHA containing at least 3HB and 3HH as monomer units, and still more preferably a gene encoding a PHA synthase capable of synthesizing a P(3HB-co-3HH) which is a copolymerized PHA of 3HB and 3HH.

Such a gene encoding a PHA synthase is, for example, preferably a gene encoding a PHA synthase derived from *Aeromonas caviae* or *Aeromonas hydrophila*, and is more preferably the gene encoding a PHA synthase derived from the *Aeromonas caviae*. Examples of the gene encoding a PHA synthase derived from the *Aeromonas caviae* include a gene encoding a protein having an amino acid sequence shown in SEQ ID NO: 1, and a gene encoding a protein which has a sequence homology of 90% or more, preferably 93% or more, more preferably 95% or more, and still more preferably 97% or more to the amino acid sequence and which has a PHA synthase activity. A specific example of the gene encoding a protein having an amino acid sequence shown in SEQ ID NO: 1 is a gene shown in SEQ ID NO: 2. A specific example of the gene encoding a protein having a sequence homology of 90% or more to the amino acid sequence shown in SEQ ID NO: 1 and having a PHA synthase activity is a gene shown in SEQ ID NO: 3.

The PHA-producing microorganism may have a gene encoding a PHA synthase derived from a genus different from the genus *Aeromonas*, in addition to the gene encoding a PHA synthase derived from the genus *Aeromonas*.

One of embodiments where the PHA-producing microorganism used in the present invention has the gene encoding a PHA synthase derived from the genus *Aeromonas* is an embodiment where the gene encoding a PHA synthase derived from the genus *Aeromonas* is introduced into a microorganism originally not having the gene encoding a PHA synthase derived from the genus *Aeromonas*. The method of introduction is not particularly limited, and any method may be selected from the following methods, or a combination of any two or more of the following methods may be used: a method of inserting the gene immediately onto a chromosome of a host, or substituting the gene onto the chromosome; a method of introducing the gene onto a megaplasmid included in a host; and a method of arranging the gene on a vector such as a plasmid, phage or phagemid to be introduced thereinto. However, any plasmid may drop out from a cell while the cell is cultured; thus, it is preferable to insert or substitute, onto a chromosome of a host, the gene encoding a PHA synthase derived from the genus *Aeromonas*. The method for each of the introduction, the insertion, the substitution, and the arrangement may be any known method. For example, a homologous recombination method or the like is usable for substituting or inserting, onto a chromosome of a host, the gene encoding a PHA synthase derived from the genus *Aeromonas*.

The gene encoding a PHA synthase derived from the genus *Aeromonas* to be introduced has on its upstream side an "expression regulatory sequence" related to the expression of the gene. The "expression regulatory sequence" in the present application may be specifically a DNA sequence positioned upstream of the start codon of the gene to control the transcriptional amount of the gene, a DNA sequence for adjusting the translational level of a messenger RNA transcribed from this gene (for example, an SD sequence (Shine Dalgarno sequence), or a DNA sequence including the two DNA sequences. As the expression regulatory sequence linked upstream of the gene encoding a PHA synthase derived from the genus *Aeromonas*, the following is usable: an expression regulatory sequence originally included in a host; any expression regulatory sequence present in the natural world; or an artificially constructed or modified expression regulatory sequence.

The expression regulatory sequence used for the gene encoding a PHA synthase derived from the genus *Aeromonas* in the microorganism of the present invention is not particularly limited. It is allowable that an expression regulatory sequence positioned upstream of the gene encoding a PHA synthase derived from the genus *Aeromonas* to be introduced is together introduced as it is; or it is allowable that when a suitable expression regulatory sequence is selected, the selected sequence is linked to the gene, and then the resultant is introduced into a host. When the gene encoding a PHA synthase derived from the genus *Aeromonas* is inserted onto the chromosome of the host, the gene may be linked to an expression regulatory sequence originally present on the host chromosome to be inserted.

The expression regulatory sequence to be selected is not particularly limited, and may be any naturally-derived expression regulatory sequence, or any variant thereof. Specifically, a promoter for regulating the transcriptional amount of the gene may be a lac promoter shown in SEQ ID NO: 4, which is a promoter derived from *E. coli*, a trp promoter shown in SEQ ID NO: 5, a lacUV5 promoter shown in SEQ ID NO: 6, which is a variant of any one of these promoters, a lacN15 promoter shown in SEQ ID NO: 7, a lacN16 promoter shown in SEQ ID NO: 8, a lacN17 promoter shown in SEQ ID NO: 9, a lacN19 promoter shown in SEQ ID NO: 10, a lacN20 promoter shown in SEQ ID NO: 11, a lacN21 promoter shown in SEQ ID NO: 12, a tad promoter shown in SEQ ID NO: 13, a tad promoter shown in SEQ ID NO: 14, a tic promoter shown in SEQ ID NO: 15, or a trc promoter shown in SEQ ID NO: 16; and may further be a REP promoter shown in SEQ ID NO: 17, which is a promoter for a phaCAB operon derived from *Cupriavidus necator*, a REPN17 promoter shown in SEQ ID NO: 18, which is a variant of the REP promoter, or a phaP1 promoter shown in SEQ ID NO: 19, which is a promoter for a phaP1 gene encoding phasin derived from *Cupriavidus necator*. These promoters are each usable as an expression regulatory sequence by linking a sequence REP-SD shown in SEQ ID NO: 20, which is an SD sequence of phaC1 gene derived from *Cupriavidus necator*, a sequence REP-SDM shown in SEQ ID NO: 21, which is a variant of the sequence REP-SD, any other known SD sequences, or any expression regulatory sequences equivalent thereto. Moreover, any other known expression regulatory sequence is also usable, examples thereof including an expression regulatory sequence PJ4a shown in SEQ ID NO: 22, which is composed of the promoter for operon including four genes of A1067, A1068, A1069 and phaJ4a derived from *Cupriavidus necator* and the SD sequence of A1067, and an expression regulatory sequence Pac shown in SEQ ID NO: 23, which is composed of the promoter for phaPCJ operon derived from *Aeromonas caviae*, and the SD sequence of phaP. Furthermore, usable is also an expression regulatory sequence obtained by modifying any one of these expression regulatory sequences with deletion, substitution and/or insertion of a base.

A second characteristic of the PHA-producing microorganism used in the present invention is that at least a portion of a PHA degrading enzyme gene has been altered by substitution, deletion, insertion, and/or addition to reduce or eliminate the activity of a PHA degrading enzyme encoded by the gene. A gene encoding a PHA degrading enzyme is also referred to as a phaZ gene, and, for example, the genus *Cupriavidus* has a plurality of phaZ genes. One example includes a PHA degrading enzyme gene shown in SEQ ID NO: 25 encoding a protein having an amino acid sequence shown in SEQ ID NO: 24, which is also referred to as a phaZd gene or phaZ6 gene. Other examples include the PHA degrading enzymes mentioned by Steinbuchel et al. (Microbiology., 156: 2136-2152 (2010)) including a phaZ1 gene having a base sequence shown in SEQ ID NO: 27 encoding a protein having an amino acid sequence shown in SEQ ID NO: 26 and a phaZ2 gene having a base sequence shown in SEQ ID NO: 29 encoding a protein having an amino acid sequence shown in SEQ ID NO: 28. Besides the genes mentioned above, other examples include genes having equivalent physiological functions. For example, mention may be made of a gene encoding a protein having a sequence homology of 90% or more to the amino acid sequence of SEQ ID NO:24, the amino acid sequence of SEQ ID NO:26, or the amino acid sequence of SEQ ID NO: 28 and having a PHA degrading enzyme activity. The sequence homology to the amino acid sequence of SEQ ID NO: 24, the amino acid sequence of SEQ ID NO: 26, or the amino acid sequence of SEQ ID NO: 28 is preferably 93% or more, more preferably 95% or more, and still more preferably 97% or more in terms of increasing the likelihood that a protein having the amino acid sequence has a PHA degrading enzyme activity.

Alteration of at least a portion of a gene by substitution, deletion, insertion, and/or addition can be accomplished by any method known to persons skilled in the art. Typical examples include a method using the mechanisms of transposons and homologous recombination (Ohman et al., J. Bacteriol., 162: 1068-1074 (1985)), and a method based on the principles of site-specific integration that occurs as a result of the machanism of homologous recombination and dropping out that occurs as a result of a second stage homologous recombination event (Noti et al., Methods Enzymol., 154: 197-217 (1987)). It is also possible to use a method in which a sacB gene derived from *Bacillus subtilis* is allowed to co-exist in a microorganism strain, and then the gene is dropped out by the second stage homologous recombination event, and thereby the microorganism strain is easily isolated as a strain resistant (Schweizer, Mol. Microbiol., 6: 1195-1204 (1992), Lenz et al., J. Bacteriol., 176: 4385-4393 (1994)). Any method of alteration by substitution, deletion, insertion, and/or addition can be used without particular limitation as long as a target PHA degrading enzyme gene on the chromosome is site-specifically disrupted or deactivated. Specifically, mention may be made of, for example, a method of deleting from the start codon to the stop codon of a PHA degrading enzyme gene on the chromosome; a method of deleting a portion of the gene sequence from the start codon to the stop codon; a method of introducing the stop codon into the gene sequence; a method of deleting the start codon; and a method of inducing a frameshift mutation by deletion or insertion. A further example is disruption of the promoter sequence of the PHA degrading enzyme gene, which results in reduced expression of the PHA degrading enzyme.

The phrase "to reduce or eliminate the activity of a PHA degrading enzyme" as used herein means that as a result of alteration of at least a portion of a gene by substitution, deletion, insertion, and/or addition, the activity of a PHA degrading enzyme encoded by the PHA degrading enzyme gene is reduced compared to the PHA degrading enzyme activity before the substitution, deletion, insertion, and/or addition, or is completely eliminated. Specifically, as a result of alteration of at least a portion of a gene by substitution, deletion, insertion, and/or addition, the activity of a PHA degrading enzyme encoded by the PHA degrading enzyme gene is preferably reduced to 20% or lower, more preferably 15% or lower, and still more preferably 10% or lower of the PHA degrading enzyme activity before the substitution, deletion, insertion, and/or addition. The complete elimination of the activity is most preferable. The percentage of reduction of the PHA degrading enzyme activity can be measured by directly measuring the PHA degrading enzyme activity, or alternatively can be estimated based on the effectiveness in suppressing a reduction of the molecular weight of produced PHA, for example.

As an example, when *Cupriavidus necator* is used as a host for a PHA-producing microorganism, the activity of the PHA degrading enzyme encoded by the phaZ6 gene is preferably reduced or eliminated, the activity of the PHA degrading enzyme encoded by the phaZ6 gene and the phaZ1 gene or the phaZ2 gene is more preferably reduced or eliminated, and the activity of the PHA degrading enzyme encoded by each of the phaZ6 gene, the phaZ1 gene, and phaZ2 gene is still more preferably reduced or eliminated. According to these aspects, a higher molecular weight PHA can be produced.

A third characteristic of the PHA-producing microorganism used in the present invention is that glycerol kinase activity is enhanced. Glycerol is taken up into a cell of a microorganism by the glycerol uptake protein. The glycerol taken up into the cell is converted to glycerol-3-phosphate by glycerol kinase. The glycerol-3-phosphate is converted to dihydroxyacetone phosphate by glycerol-3-phosphate dehydrogenase and is assimilated through a glycolysis system. The enhancement of the glycerol kinase activity in the present invention refers to a case where the glycerol kinase activity is newly imparted to a host originally not having the glycerol kinase activity by a method as described later, or a case where the glycerol kinase activity of a host originally having the glycerol kinase activity is enhanced and the glycerol kinase activity increases as compared with that before the enhancement, and the specific means is not particularly limited as long as PHA can have a high molecular weight which is an object of the present invention. When the glycerol kinase activity of the host originally having the glycerol kinase activity is enhanced, specifically, the glycerol kinase activity is preferably 1.2 times or more, and more preferably 1.5 times or more than that before the enhancement. The percentage of enhancement of the glycerol kinase activity can be measured by directly measuring the glycerol kinase activity or alternatively can be estimated based on the effectiveness in suppressing a reduction of the molecular weight of produced PHA, for example.

Examples of the method of enhancing the glycerol kinase activity include a method of introducing a gene encoding exogenous glycerol kinase and a method of enhancing an endogenous glycerol kinase activity inherent in the host of the PHA-producing microorganism.

The method of introducing a gene encoding exogenous glycerol kinase is not particularly limited, and any method may be selected from the following methods, or a combination of any two or more of the following methods may be used: a method of inserting the gene immediately onto a chromosome of a host, or substituting the gene onto the chromosome; a method of introducing the gene onto a megaplasmid included in a host; and a method of arranging the gene on a vector such as a plasmid, phage or phagemid to be introduced thereinto. However, any plasmid may drop out from a cell while the cell is cultured; thus, it is preferable to insert or substitute the gene encoding exogenous glycerol kinase onto a chromosome of a host. The method for each of the introduction, the insertion, the substitution, and the arrangement may be any known method. For example, a homologous recombination method or the like is usable for substituting or inserting, onto a chromosome of a host, the gene encoding exogenous glycerol kinase.

In the present invention, the gene encoding exogenous glycerol kinase to be introduced into a PHA-producing microorganism is not particularly limited. For example, it is possible to use a gene encoding glycerol kinase derived from the genus *Escherichia*, genus *Salmonella*, genus *Yersinia*, genus *Serratia*, genus *Pectobacterium*, genus *Shigella*, genus *Enterobacter*, genus Cronobacter, genus *Klebsiella*, genus *Erwinia*, genus *Haemophilus*, genus *Pasteurella*, genus Mannheimia, genus Xylella, genus *Xanthomonas*, genus *Vibrio*, genus *Pseudomonas*, genus *Francisella*, genus *Aeromonas*, genus *Ralstonia*, genus *Rhodopseudomonas*, genus Chromobacterium, genus *Burkholderia*, genus *Bacillus*, genus *Staphylococcus*, genus *Listeria*, genus *Lactococcus*, genus *Streptococcus*, genus *Lactobacillus*, genus Entericoccus, genus *Clostridium*, genus *Thermoanaerobacter*, genus *Mycoplasma*, genus *Mycobacterium*, genus *Corynebacterium*, genus *Streptomyces*, genus *Borrelia*, genus Leptospira, or genus *Cupriavidus*, or genes each encoding a variant thereof. In the present invention, the gene encoding glycerol kinase is more preferably a gene encoding glycerol kinase derived from the genus *Escherichia*, still more preferably a gene encoding glycerol kinase derived from *Escherichia coli*, and particularly preferably a gene encoding a protein having an amino acid sequence shown in SEQ ID NO: 30 or a gene encoding a protein which has a sequence homology of 90% or more, preferably 93% or more, more preferably 95% or more, and still more preferably 97% or more to the amino acid sequence and which has a glycerol kinase activity. An example of the gene encoding a protein having an amino acid sequence shown in SEQ ID NO: 30 is a gene shown in SEQ ID NO: 31 derived from *Escherichia coli.*

The gene encoding exogenous glycerol kinase to be introduced preferably has on its upstream side an expression regulatory sequence related to the expression of the gene. As the expression regulatory sequence linked upstream of the gene encoding exogenous glycerol kinase, the following is usable: an expression regulatory sequence originally included in a host; any expression regulatory sequence present in the natural world; or an artificially constructed or modified expression regulatory sequence.

The expression regulatory sequence used for the gene encoding exogenous glycerol kinase in the present invention is not particularly limited. It is allowable that an expression regulatory sequence positioned upstream of the gene encoding exogenous glycerol kinase to be introduced is together introduced as it is; or it is allowable that when a suitable expression regulatory sequence is selected, the selected sequence is linked to the gene, and then the resultant is introduced into a host. When the gene encoding exogenous glycerol kinase is inserted onto the chromosome of the host, the gene may be linked to an expression regulatory sequence originally present on the host chromosome to be inserted. As the expression regulatory sequence to be selected herein, the expression regulatory sequence as described above with respect to the gene encoding a PHA synthase can be used.

The method of enhancing the endogenous glycerol kinase activity inherent in the host of the PHA-producing microorganism is not particularly limited. The above-mentioned expression regulatory sequence may be inserted upstream of a gene encoding endogenous glycerol kinase on a chromosome, an expression level may be increased by introducing a copy of the gene encoding endogenous glycerol kinase at a position different from the position where the copy of the gene encoding endogenous glycerol kinase is originally present, or a glycerol kinase activity may be increased by a gene encoding endogenous glycerol kinase with introduction of a mutation into the gene. These methods may be combined or used together.

In the present invention, the gene encoding endogenous glycerol kinase refers to a gene identified as encoding glycerol kinase in the genomic information of the host or a gene encoding a protein known to have a glycerol kinase activity. For example, when a *Cupriavidus necator* H16 strain is used as the host of the PHA-producing microorganism, examples thereof include an h16_A2507 gene having a base sequence shown in SEQ ID NO: 33 encoding a protein having an amino acid sequence shown in SEQ ID NO: 32 and an h16_B1199 gene having a base sequence shown in SEQ ID NO: 35 encoding a protein having an amino acid sequence shown in SEQ ID NO: 34.

When an expression regulatory sequence is inserted upstream of the gene encoding endogenous glycerol kinase on the chromosome, a known method can be used, and, for example, a homologous recombination method or the like can be used. As the expression regulatory sequence, the expression regulatory sequence described above with respect to the gene encoding a PHA synthase can be used.

When a copy of the gene encoding endogenous glycerol kinase is introduced at a position different from the position where the copy of the gene encoding endogenous glycerol kinase is originally present, the introduction method is not particularly limited, and any method may be selected from the following methods, or a combination of any two or more of the following methods may be used: a method of inserting a copy of the gene immediately onto a chromosome of a host, or substituting a copy of the gene onto the chromosome; a method of introducing a copy of the gene onto a megaplasmid included in a host; and a method of arranging a copy of the gene on a vector such as a plasmid, phage or phagemid to be introduced thereinto. However, any plasmid may drop out from a cell while the cell is cultured; thus, it is preferable to insert or substitute, onto a chromosome of a host, a copy of the gene encoding endogenous glycerol kinase. The method for each of the introduction, the insertion, the substitution, and the arrangement may be any known method. For example, a homologous recombination method or the like is usable for substituting or inserting, onto a chromosome of a host, a copy of the gene encoding endogenous glycerol kinase.

A copy of the gene encoding endogenous glycerol kinase to be introduced preferably has on its upstream side an expression regulatory sequence related to the expression of the copy of the gene. As the expression regulatory sequence linked upstream of the gene encoding endogenous glycerol kinase, the following is usable: an expression regulatory sequence originally included in a host; any expression regulatory sequence present in the natural world; or an artificially constructed or modified expression regulatory sequence.

The expression regulatory sequence used for the gene encoding endogenous glycerol kinase in the present invention is not particularly limited. It is allowable that an expression regulatory sequence positioned upstream of the gene encoding endogenous glycerol kinase is together introduced as it is; or it is allowable that when a suitable expression regulatory sequence is selected, the selected sequence is linked to the gene, and then the resultant is introduced into a host. When a copy of the gene encoding endogenous glycerol kinase is inserted onto the chromosome of the host, the copy of the gene may be linked to an expression regulatory sequence originally present on the host chromosome to be inserted. As the expression regulatory sequence to be selected herein, the expression regulatory sequence as described above with respect to the gene encoding a PHA synthase can be used.

When a mutation is introduced into the gene encoding endogenous glycerol kinase, any known method can be used. For example, a gene encoding glycerol kinase is used as a template to conduct error-prone PCR or PCR using a primer into which a mutation has been introduced, whereby the gene encoding glycerol kinase into which a mutation has been introduced can be obtained.

Preferably, the PHA-producing microorganism of the present invention is not enhanced in glycerol uptake activity into cells. According to this aspect, a higher molecular weight PHA can be produced. An example of a gene encoding a glycerol uptake protein is a gene referred to as glpF, examples thereof include a gene represented by a base sequence shown in SEQ ID NO: 37 encoding a protein having an amino acid sequence shown in SEQ ID NO: 36 and a gene represented by a base sequence shown in SEQ ID NO: 39 encoding a protein having an amino acid sequence shown in SEQ ID NO: 38. When the PHA-producing microorganism has, on the genome, a gene corresponding to glpF as a gene encoding a glycerol uptake protein into cells, it is preferable not to enhance the glycerol uptake activity by genetic manipulation. In addition, it is preferable not to introduce an exogenous gene encoding a glycerol uptake protein into cells or a gene encoding a variant thereof into the PHA-producing microorganism by genetic manipulation.

As the host of the PHA-producing microorganism of the present invention, a PHA-producing microorganism having a PHA degrading enzyme gene can be used. Examples of such a PHA-producing microorganism as the host include microorganisms belonging to the genus *Cupriavidus*, with *Cupriavidus necator* being preferred, and a *Cupriavidus necator* H16 strain being more preferred. Here, mutant strains obtained through artificial mutation of the microorganism, and mutant bacterial strains obtained through genetic engineering can be used.

In the present invention, by culturing the PHA-producing microorganism of the present invention, PHA can be produced by the microorganism. As a method of culturing the PHA-producing microorganism of the present invention, it is possible to use a conventional method of culturing a microorganism, and the culture may performed by adding a suitable carbon source to a medium.

At the time of culture, any carbon sources may be used as long as the PHA-producing microorganisms of the present invention are assimilable. Preferable examples thereof include saccharides such as glucose, fructose, and sucrose; oils and fats such as palm oil, palm kernel oil, corn oil, coconut oil, olive oil, soybean oil, rapeseed oil, Jatropha oil, fractionated products of any oils and fats, and refined by-products of any oils and fats; fatty acids such as lauric acid, oleic acid, stearic acid, palmitic acid, and myristic acid, and derivatives of the fatty acids; and glycerol. In the present invention, since the effect of enhancing the molecular weight of PHA is obtained by enhancing the glycerol kinase activity, it is more preferable to use a carbon source containing glycerol and/or a compound containing a glycerol skeleton, it is still more preferable to use glycerol and/or oils and fats and fractionated products thereof, and it is particularly preferable to use glycerol; a mixture of glycerol and other carbon sources; vegetable oils and fats such as palm oil and palm kernel oil; and palm olein, palm double olein or palm kernel olein, which is a low-melting-point fraction obtained by fractionating palm oil or palm kernel oil.

In the production of PHA according to the present invention, the microorganisms are preferably cultured using a medium containing the carbon sources, nitrogen sources which are nutrients other than the carbon sources, inorganic salts, and other organic nutrients. Examples of the nitrogen sources include peptone, meat extract, and yeast extract, in addition to ammonium salts such as ammonia, ammonium chloride, ammonium sulfate, and ammonium phosphate. Examples of the inorganic salts include potassium dihydrogenphosphate, disodium hydrogen phosphate, magnesium phosphate, magnesium sulfate, and sodium chloride. Examples of the other organic nutrients include amino acids such as glycine, alanine, serine, threonine, and proline, and vitamins such as vitamin B1, vitamin B12, and vitamin C.

The conditions for culturing the microorganisms, such as culture temperature, culture time, pH during culture, and medium, may be the same as those generally used for culturing microorganisms used.

The PHA produced in the present invention is not particularly limited as long as it is PHA produced by a microorganism. A homopolymerized PHA of a 3-hydroxyalkanoic acid selected from 3-hydroxyalkanoic acids having 4 to 16 carbon atoms, and a copolymerized PHA obtained by copolymerizing one or more 3-hydroxyalkanoic acids selected from 3-hydroxyalkanoic acids having 4 to 16 carbon atoms are preferable. Examples thereof include P(3HB), P(3HB-co-3HV), P(3HB-co-3HH), and P(3HB-co-4HB). Preferred is a copolymerized PHA containing a structural unit derived from 3-hydroxybutyric acid, and more preferred is a copolymerized PHA containing a structural unit derived from at least 3-hydroxybutyric acid and 3-hydroxyhexanoic acid.

In the present invention, the method of collecting PHA from cell bodies is not particularly limited, and for example, the following method may be used. After the termination of the culture, a centrifugal separator or the like is used to separate the cell bodies from the culture solution. The cell bodies are washed with distillated water, methanol or the like, and dried. From the dried cell bodies, an organic solvent such as chloroform is used to extract the PHA. Form this PHA-containing organic solvent solution, cell body components are removed by filtration or the like, and a poor solvent such as methanol or hexane is added to the filtrate to precipitate the PHA. Furthermore, filtration or centrifugal separation is used to remove the supernatant, and the remnant is then dried to collect the PHA.

The method of measuring the molecular weight of the PHA produced in the present invention is not particularly limited, and for example, the following method may be used. A gel permeation chromatography method is used to analyze the molecular weight of the PHA. Ten milligrams of the purified PHA is dissolved in 10 ml of chloroform, and the solution is filtered through a 0.2-mm filter to prepare a measurement sample. An amount of 0.05 ml of the sample is analyzed. The measurement is performed at 40° C. using a measurement system SCL-10A (available from SHIMADZU CORPORATION) and two Shodex GPC K-806L columns (available from Showa Denko K.K.) connected in series. The mobile phase is chloroform (1.0 ml/min), and an RI detector (RID-10A, available from SHIMADZU CORPORATION) is used. Polystyrenes treated in a similar manner (available from Showa Denko K.K., weight average molecular weight: 7,110,000, 1,920,000, 668,000, 197,000, 31,400, 2,950) are used as standard samples, and the weight average molecular weight of the PHA is determined from the calibration curve.

The molecular weight of the PHA produced in the present invention is not particularly limited. Regarding the molecular weight after cultivation has ended, the weight average molecular weight is preferably from 300,000 to 4,000,000, more preferably 500,000 to 3,500,000, still more preferably 700,000 to 3,300,000, and particularly preferably 1,000,000 to 3,000,000.

The PHA produced in the present invention may contain additives such as a crystal nucleating agent, an antioxidant, an ultraviolet absorbent, colorants such as a dye and a pigment, a plasticizer, a lubricant, an inorganic filler, an antistatic agent, an anti-mold agent, an antibacterial agent, a foaming agent, and a flame retardant, as needed.

A resin composition including the PHA produced by the present invention can be formed/worked to produce a molded article. The method of the forming/working may be a method known in the prior art, such as injection molding, film molding, blow molding, fiber spinning, extrusion foaming, or bead foaming.

The molded article is usable for, for example, various containers, packaging members, films for agriculture and horticulture, and medical materials.

EXAMPLES

Hereinafter, the present invention will be more specifically described by way of examples. However, the invention is not limited to these examples at all. Any genetic manipulation described in the examples can be attained by methods described in Molecular Cloning (Cold Spring Harbor Laboratory Press, 1989). Any enzyme, any cloning host and any other that are used in the genetic manipulation are commercially available from suppliers in the market, and are usable in accordance with the instructions given by the suppliers. Any enzyme used in the examples is not particularly limited as long as the enzyme is usable in genetic manipulation.

(Production Example 1) Preparation of Plasmid pCUP2-PlacN17-glpK$_{Ec}$ for Enhancing Glycerol Kinase Activity A plasmid pCUP2-PlacN17-glpK$_{Ec}$ for enhancing glycerol kinase activity was prepared.

First, a product pCR(R)2.1-TOPO(R) (available from Invitrogen) was used as a template to conduct PCR using respective DNAs represented by SEQ ID NOs: 40 and 41 as primers. In a similar manner, PCR was conducted using respective DNAs represented by SEQ ID NOs: 42 and 43 as primers. Next, a genomic DNA of *Escherichia coli* HB101 strain was used as a template to conduct PCR using respective DNAs represented by SEQ ID NOs: 44 and 45 as primers. Furthermore, the three DNA fragments obtained by the PCR were used as templates to conduct PCR using respective DNAs represented by SEQ ID NOs: 40 and 45 as primers. The resultant DNA fragment was ligated with a DNA fragment obtained by digesting the pCUP2 vector described in JP 2007-259708 A with MunI and SpeI, using In-Fusion(R) HD Cloning Kit (available from Takara Bio Inc.) to prepare a plasmid pCUP2-PlacN17-glpK$_{Ec}$ for enhancing glycerol kinase having an expression regulatory sequence composed of a lacN17 promotor and a phaC1SD sequence and having a glpK$_{Ec}$ structural gene sequence.

(Production Example 2) Preparation of Plasmid Introduced Strain for Enhancing Glycerol Kinase Activity, Using KNK-005 ΔphaZ1,2,6 Strain as Parent Strain For the purpose of preparing a bacterial strain in which the glycerol kinase activity was enhanced, the KNK-005 ΔphaZ1,2,6 strain (see WO 2015/146195) was used as a parent strain to prepare a bacterial strain into which the plasmid described in Production Example 1 was introduced. The KNK-005 ΔphaZ1,2,6 strain is a bacterial strain in which the entire length of the phaZ1 gene and that of the phaZ6 gene on any chromosome are deleted, a sequence from the 16th codon of the phaZ2 gene to the stop codon thereof is deleted, and the chromosome has, thereon, a gene encoding a PHA synthase shown in SEQ ID NO: 3.

First, the KNK-005 ΔphaZ1,2,6 strain was cultured overnight in a nutrient broth medium (available from Difco Laboratories). Into 50 ml of the nutrient broth medium was inoculated 0.5 ml of the resultant culture liquid, and then the strain was cultured at 30° C. for 3 hours. The resultant culture liquid was rapidly cooled on ice. The cell bodies were collected and sufficiently washed with ice-cooled distilled water. Thereafter, the resultant cell bodies were suspended in 2 ml of distilled water. The suspended cell body liquid was mixed with a plasmid solution. The mixture was poured into a cuvette to be electroporated. The electroporation was performed, using a Micro Pulser Electroporator (available from Bio-Rad Laboratories, Inc.) under conditions of a voltage of 1.5 kV, a resistance of 800Ω, and a current of 25 μF. After the electroporation, the cell body solution was collected, and thereto was added 5 ml of the nutrient broth medium to culture the cell bodies at 30° C. for 3 hours. The resultant culture liquid was applied to a Nutrient Agar (available from DIFCO Laboratories) containing 100 mg/L of kanamycin sulfate. This was cultured at 30° C. for 3 days, and from the resultant colonies, a bacterial strain into which the plasmid was introduced was obtained.

The resultant bacterial strain was named a KNK-005 ΔphaZ1,2,6/pCUP2-PlacN17-glp$K_{Ec}$ strain.

(Production Example 3) Preparation of Plasmid Introduced Strain for Enhancing Glycerol Kinase Activity, Using KNK-005 REP-phaJ4b ΔphaZ1::Plac-pha$C_{Re}$ ΔZ,2,6 Strain as Parent Strain For the purpose of preparing a bacterial strain in which the glycerol kinase activity was enhanced, the KNK-005 REP-phaJ4b ΔphaZ1::Plac-pha$C_{Re}$ ΔZ,2,6 strain (see WO 2015/146195) was used as a parent strain to prepare a bacterial strain into which the plasmid described in Production Example 1 was introduced in the same manner as in Production Example 2. The KNK-005 REP-phaJ4b ΔphaZ1::Plac-pha$C_{Re}$ ΔZ,2,6 strain is a bacterial strain in which the entire length of the phaZ1 gene and that of the phaZ6 gene on any chromosome are deleted, a sequence from the 16th codon of the phaZ2 gene to the stop codon thereof is deleted, an expression regulatory sequence composed of a REP promoter and a phaC1SD(REP-SD) sequence is inserted immediately upstream of the phaJ4b gene, a lac promoter, a phaC1SD(REP-SD) sequence, and a pha$C_{Re}$ structural gene sequence are inserted into the phaZ1-gene-deleted region, and the chromosome has, thereon, a gene encoding a PHA synthase of SEQ ID NO: 3. The resultant bacterial strain was named a KNK-005 REP-phaJ4b ΔphaZ1::Plac-pha$C_{Re}$ ΔZ,2,6/pCUP2-PlacN17-glp$K_{Ec}$ strain.

(Production Example 4) Preparation of KNK-005 REP-phaJ4b ΔphaZ1::Plac-pha$C_{Re}$ ΔphaZ6::Plac-glp$K_{Ec}$ ΔZ,2 Strain For the purpose of introducing a gene expression cassette for enhancing the glycerol kinase activity into the phaZ6-gene-deleted region of the KNK-005 REP-phaJ4b ΔphaZ1::Plac-pha$C_{Re}$ ΔZ,2,6 strain, a DNA-inserting plasmid was prepared.

First, a product pCR(R)2.1-TOPO(R) was used as a template to conduct PCR using respective DNAs represented by SEQ ID NOs: 40 and 43 as primers. Next, a genomic DNA of *Escherichia coli* HB101 strain was used as a template to conduct PCR using respective DNAs represented by SEQ ID NOs: 44 and 45 as primers. Furthermore, the two DNA fragments obtained by the PCR were used as templates to conduct PCR using respective DNAs represented by SEQ ID NOs: 40 and 45 as primers. The resultant DNA fragment was ligated with a DNA fragment obtained by digesting a pCUP2 vector with MunI and SpeI, using In-Fusion(R) HD Cloning Kit to prepare a plasmid pCUP2-Plac-glp$K_{ec}$ having an expression regulatory sequence composed of a lac promotor and a phaC1SD sequence and having a glp$K_{Ec}$ structural gene sequence.

Next, a genomic DNA of *C. necator* H16 strain was used as a template to conduct PCR using respective DNAs represented by SEQ ID NOs: 46 and 47 as primers. In a similar manner, PCR was conducted using respective DNAs represented by SEQ ID NOs: 48 and 49 as primers. The two DNA fragments obtained by the PCR were used as templates to conduct PCR using respective DNAs represented by SEQ ID NOs: 46 and 49 as primers, and the resultant fragment was digested with SmiI. This DNA fragment was ligated with a DNA fragment obtained by digesting the vector pNS2X-sacB described in JP 2007-259708 A with SmiI, using a DNA ligase to prepare a DNA-inserting plasmid pNS2X-sacB-dZ6UL having a DNA sequence at the upstream side of the phaZ6 structural gene, a DNA sequence shown in SEQ ID NO: 50, and a DNA sequence at the downstream side of the phaZ6 structural gene.

Next, the pCUP2-Plac-glp$K_{Ec}$ was used as a template to conduct PCR using respective DNAs represented by SEQ ID NOs: 51 and 45 as primers, and the resultant fragment was digested with EcoRI and SpeI. This DNA fragment was ligated with a DNA fragment obtained by digesting pNS2X-sacB-dZ6UL with MunI and SpeI, using a DNA ligase to prepare a DNA-inserting plasmid pNS2X-sacB-dZ6UL-Plac-glp$K_{Ec}$ having a DNA sequence at the upstream side of the phaZ6 structural gene, an expression regulatory sequence composed of a lac promoter and a phaC1SD(REP-SD) sequence, a glp$K_{Ec}$ structural gene sequence, and a DNA sequence at the downstream side of the phaZ6 structural gene.

Next, the KNK-005 REP-phaJ4b ΔphaZ1::Plac-pha$C_{Re}$ ΔZ,2,6 strain was used as a parent strain to prepare a strain in which a gene expression cassette for enhancing the glycerol kinase activity was inserted into the phaZ6-gene-deleted region using pNS2X-sacB-dZ6UL-Plac-glp$K_{Ec}$. pNS2X-sacB-dZ6UL-Plac-glp$K_{Ec}$ was introduced into an *E. coli S*17-1 strain (ATCC47055). The *E. coli* strain and a KNK-005 REP-phaJ4b ΔphaZ1::Plac-pha$C_{Re}$ ΔZ,2,6 strain were mix-cultured on a nutrient agar medium to be subjected to conjugal transfer.

The bacterial strain grown on Simmons' agar medium containing 250 mg/L of kanamycin sulfate (2 g/L of sodium citrate, 5 g/L of sodium chloride, 0.2 g/L of magnesium sulfate heptahydrate, 1 g/L of ammonium dihydrogenphosphate, 1 g/L of dipotassium hydrogenphosphate, and 15 g/L of agar; pH: 6.8) was selected from bacterial strains after the conjugal transfer, and a strain in which the plasmid was introduced onto the chromosome of the KNK-005 REP-phaJ4bΔphaZ1::Plac-pha$C_{Re}$ ΔZ,2,6 strain was obtained. This strain was cultured for two generations in a nutrient broth medium, and then bacterial strains growing on a nutrient agar medium containing 20% of sucrose were selected therefrom. From the resultant bacterial strains, PCR was used to screen strains in which the gene expression cassette for enhancing the glycerol kinase activity was inserted into the phaZ6-gene-deleted region. One of the strains was named a KNK-005 REP-phaJ4b ΔphaZ1::Plac-pha$C_{Re}$ ΔphaZ6::Plac-glp$K_{Ec}$ ΔZ,2 strain. The KNK-005 REP-phaJ4b ΔphaZ1::Plac-pha$C_{Re}$ ΔphaZ6::Plac-glp$K_{Ec}$ ΔZ,2 strain is a bacterial strain in which a lac promoter, a phaC1SD(REP-SD) sequence, and a glp$K_{Ec}$ structural gene sequence are inserted into the phaZ6-gene-deleted region of the KNK-005 REP-phaJ4b ΔphaZ1::Plac-pha$C_{Re}$ ΔZ,2,6 strain.

(Production Example 5) Preparation of KNK-005 REP-phaJ4b ΔphaZ1::Plac-pha$C_{Re}$ ΔphaZ6::PlacN17-glp$K_{Ec}$ ΔZ,2 Strain For the purpose of introducing a gene expression cassette for enhancing the glycerol kinase activity into the phaZ6-gene-deleted region of the KNK-005 REP-phaJ4b ΔphaZ1::Plac-pha$C_{Re}$ ΔZ,2,6 strain, a DNA-inserting plasmid was prepared.

First, the pCUP2-PlacN17-glp$K_{Ec}$ prepared in Production Example 1 was used as a template to conduct PCR using respective DNAs represented by SEQ ID NOs: 51 and 45 as primers, and the resultant fragment was digested with EcoRI and SpeI. This DNA fragment was ligated with a DNA fragment obtained by digesting the pNS2X-sacB-dZ6UL prepared in Production Example 4 with MunI and SpeI, using a DNA ligase to prepare a DNA-inserting plasmid pNS2X-sacB-dZ6UL-PlacN17-glp$K_{Ec}$ having a DNA sequence at the upstream side of the phaZ6 structural gene, an expression regulatory sequence composed of a lacN17 promoter and a phaC1SD(REP-SD) sequence, a glp$K_{Ec}$ structural gene sequence, and a DNA sequence at the downstream side of the phaZ6 structural gene.

Next, in the same manner as in Production Example 4, the KNK-005 REP-phaJ4b ΔphaZ1::Plac-pha$C_{Re}$ ΔZ,2,6 strain was used as a parent strain to prepare a strain in which a gene expression cassette for enhancing the glycerol kinase activity was inserted into the phaZ6-gene-deleted region using pNS2X-sacB-dZ6UL-PlacN17-glp$K_{Ec}$. The resultant strain was named a KNK-005 REP-phaJ4b ΔphaZ1::Plac-pha$C_{Re}$ ΔphaZ6::PlacN17-glp$K_{Ec}$ ΔZ,2 strain. The KNK-005 REP-phaJ4b ΔphaZ1::Plac-pha$C_{Re}$ ΔphaZ6::PlacN17-glp$K_{Ec}$ ΔZ,2 strain is a bacterial strain in which a lacN17 promoter, a phaC1SD(REP-SD) sequence, and a glp$K_{Ec}$ structural gene sequence are inserted into the phaZ6-gene-deleted region of the KNK-005 REP-phaJ4b ΔphaZ1::Plac-pha$C_{Re}$ ΔZ,2,6 strain.

(Production Example 6) Preparation of KNK-005 REP-phaJ4b PlacUV5-A2507 ΔphaZ1::Plac-pha$C_{Re}$ ΔZ,2,6 Strain For the purpose of inserting an expression regulatory sequence for enhancing the expression of h16_A2507 upstream of the h16_A2507 gene on the chromosome, a plasmid for inserting an expression regulatory sequence was prepared.

First, a genomic DNA of *C. necator* H16 strain was used as a template to conduct PCR using respective DNAs represented by SEQ ID NOs: 52 and 53 as primers. In a similar manner, PCR was conducted using respective DNAs represented by SEQ ID NOs: 54 and 55 as primers. Furthermore, the pCUP2-Plac-glp$K_{Ec}$ prepared in Production Example 4 was used as a template to conduct PCR using respective DNAs represented by SEQ ID NOs: 56 and 57 as primers. In a similar manner, PCR was conducted using respective DNAs represented by SEQ ID NOs: 58 and 59 as primers. The four DNA fragments obtained by the PCR were used as templates to conduct PCR using respective DNAs represented by SEQ ID NOs: 52 and 55 as primers, and the resultant fragment was digested with SmiI. This DNA fragment was ligated with a DNA fragment obtained by digesting pNS2X-sacB with SmiI, using a DNA ligase to prepare a DNA-inserting plasmid pNS2X-sacB-A2507U-PlacUV5-A2507 having a DNA sequence at the upstream side of the h16_A2507 structural gene, an expression regulatory sequence composed of a lacUV5 promoter and a phaC1SD sequence, and a portion of a h16_A2507 structural gene sequence.

Next, in the same manner as in Production Example 4, the KNK-005 REP-phaJ4b ΔphaZ1::Plac-pha$C_{Re}$ ΔZ,2,6 strain was used as a parent strain, and an expression regulatory sequence was inserted upstream of the h16_A2507 gene using pNS2X-sacB-A2507U-PlacUV5-A2507. The resultant strain was named a KNK-005 REP-phaJ4b PlacUV5-A2507 ΔphaZ1::Plac-pha$C_{Re}$ ΔZ,2,6 strain. The KNK-005 REP-phaJ4b PlacUV5-A2507 ΔphaZ1::Plac-pha$C_{Re}$ ΔZ,2,6 strain is a bacterial strain in which an expression regulatory sequence composed of a lacUV5 promoter and a phaC1SD sequence is inserted immediately upstream of the h16_A2507 gene of the KNK-005 REP-phaJ4b ΔphaZ1::Plac-pha$C_{Re}$ ΔZ,2,6 strain.

(Production Example 7) Preparation of KNK-005 REP-phaJ4b ΔphaZ1::Plac-pha$C_{Re}$ ΔphaZ6::PlacUV5-A2507 ΔZ,2 Strain For the purpose of introducing a gene expression cassette for enhancing the glycerol kinase activity into the phaZ6-gene-deleted region of the KNK-005 REP-phaJ4b ΔphaZ1::Plac-pha$C_{Re}$ ΔZ2,6 strain, a DNA-inserting plasmid was prepared.

First, the pNS2X-sacB-A2507U-PlacUV5-A2507 prepared in Production Example 6 was used as a template to conduct PCR using respective DNAs represented by SEQ ID NOs: 40 and 43 as primers. Next, a genomic DNA of *C. necator* H16 strain was used as a template to conduct PCR using respective DNAs represented by SEQ ID NOs: 60 and 61 as primers. Furthermore, the two DNA fragments obtained by the PCR were used as templates to conduct PCR using respective DNAs represented by SEQ ID NOs: 40 and 61 as primers. The resultant DNA fragment was ligated with a DNA fragment obtained by digesting a pCUP2 vector with MunI and SpeI, using In-Fusion(R) HD Cloning Kit to prepare a plasmid pCUP2-PlacUV5-A2507 having an expression regulatory sequence composed of a lacUV5 promotor and a phaC1SD sequence and having a h16_A2507 structural gene sequence.

Next, the pCUP2-PlacUV5-A2507 was used as a template to conduct PCR using respective DNAs represented by SEQ ID NOs: 51 and 61 as primers, and the resultant fragment was digested with EcoRI and SpeI. This DNA fragment was ligated with a DNA fragment obtained by digesting the pNS2X-sacB-dZ6UL prepared in Production Example 4 with MunI and SpeI, using a DNA ligase to prepare a DNA-inserting plasmid pNS2X-sacB-dZ6UL-PlacUV5-A2507 having a DNA sequence at the upstream side of the phaZ6 structural gene, an expression regulatory sequence composed of a lacUV5 promoter and a phaC1SD sequence, a h16_A2507 structural gene sequence, and a DNA sequence at the downstream side of the phaZ6 structural gene.

Next, in the same manner as in Production Example 4, the KNK-005 REP-phaJ4b ΔphaZ1::Plac-pha$C_{Re}$ ΔZ2,6 strain was used as a parent strain to prepare a strain in which a gene expression cassette for enhancing the glycerol kinase activity was inserted into the phaZ6-gene-deleted region using pNS2X-sacB-dZ6UL-PlacUV5-A2507. The resultant strain was named a KNK-005 REP-phaJ4b ΔphaZ1::Plac-pha$C_{Re}$ ΔphaZ6::PlacUV5-A2507 ΔZ,2 strain. The KNK-005 REP-phaJ4b ΔphaZ1::Plac-pha$C_{Re}$ ΔphaZ6::PlacUV5-A2507 ΔZ,2 strain is a bacterial strain in which a lacUV5 promoter, a phaC1SD(REP-SD) sequence, and a h16_A2507 structural gene sequence are inserted into the phaZ6-gene-deleted region of the KNK-005 REP-phaJ4b ΔphaZ1::Plac-pha$C_{Re}$ ΔZ,2,6 strain.

(Example 1) Production of PHA by KNK-005 ΔphaZ1,2,6/pCUP2-PlacN17-glp$K_{Ec}$ Strain The KNK-005 ΔphaZ1,2,6/pCUP2-PlacN17-glp$K_{Ec}$ strain obtained in Production Example 2 was cultured and purified under the following conditions, and the PHA production amount was calculated. The weight average molecular weight of the resultant PHA was measured. The PHA production amount was 11.8 g/L, and the weight average molecular weight was $217\times10^4$. The results obtained are shown in Table 1.

<Culture>

The bacterial strain was cultured as follows.

The composition of a seed medium was: 1% (w/v) Meat extract, 1% (w/v) Bacto Trypton, 0.2% (w/v) Yeast extract, 0.9% (w/v) $Na_2HPO_4.12H_2O$, 0.15% (w/v) $KH_2PO_4$ (pH 6.8), and $5\times10^{-6}$% (w/v) kanamycin.

The composition of the PHA-producing medium was: 1.1% (w/v) $Na_2HPO_4.12H_2O$, 0.19% (w/v) $KH_2PO_4$, 0.13% (w/v) $(NH_4)_2SO_4$, 0.1% (w/v) $MgSO_4.7H_2O$, 0.1% (v/v) trace metal salt solution (prepared by dissolving, in 0.1 N hydrochloric acid, 1.6% (w/v) $FeCl_3.6H_2O$, 1% (w/v) $CaCl_2.2H_2O$, 0.02% (w/v) $CoCl_2.6H_2O$, 0.016% (w/v) $CuSO_4.5H_2O$, and 0.012% (w/v) $NiCl_2.6H_2O$). As the carbon source, oleic acid and glycerol were used at a concentration of 1.0% (w/v), respectively.

A bacterial strain was inoculated into 10 ml of a seed medium and cultured at a culture temperature of 30° C. for 17 hours to obtain a preculture solution.

Next, the preculture solution was inoculated into a shake flask containing 50 ml of the PHA-producing medium to a concentration of 1.0% (v/v), and cultured with shaking at a culture temperature of 30° C. for 72 hours.

<Purification>

After the culturing was ended, the cell bodies were collected by centrifugation, washed with ethanol, and then vacuum-dried to give dry cell bodies.

To 1 g of the resultant dry cell bodies was added chloroform in an amount of 100 ml. At room temperature, the resultant was stirred a whole day and night. PHA in the cell bodies was extracted. The cell body residue was filtrated off, and then an evaporator was used to concentrate the PHAs to a total volume of 30 ml. Thereafter, 90 ml of hexane was gradually added, and then the resultant was gently stirred for 1 hour. The precipitated PHAs were separated by filtration, and then vacuum-dried at 60° C. for 3 hours to give the PHAs as dried PHAs. The weight of the resultant dried PHA was measured, and the PHA production amount was calculated.

<Weight Average Molecular Weight Measurement>

A gel permeation chromatography method was used to analyze the weight average molecular weight of the PHA. Ten milligrams of the purified PHA was dissolved in 10 ml of chloroform, and the solution was filtered through a 0.2-mm filter to prepare a measurement sample. An amount of 0.05 ml of the sample was analyzed. The measurement was performed at 40° C. using a measurement system SCL-10A (available from SHIMADZU CORPORATION) and two Shodex GPC K-806L columns (available from Showa Denko K.K.) connected in series. The mobile phase was chloroform (1.0 ml/min), and an RI detector (RID-10A, available from SHIMADZU CORPORATION) was used. Polystyrenes treated in a similar manner (available from Showa Denko K.K., weight average molecular weight: 7,110,000, 1,920,000, 668,000, 197,000, 31,400, 2,950) were used as standard samples, and the weight average molecular weight of the PHA was determined from the calibration curve.

(Comparative Example 1) Production of PHA by KNK-005 Strain

PHA was produced by the same method as in Example 1, using the KNK-005 strain (see U.S. Pat. No. 7,384,766) instead of the KNK-005 ΔphaZ1,2,6/pCUP2-PlacN17-glpK$_{Ec}$ strain, and the production amount and weight average molecular weight of the resultant PHA were measured. However, no kanamycin was added to the seed medium. The KNK-005 strain is a bacterial strain having, on the chromosome, the gene encoding a PHA synthase shown in SEQ ID NO: 3. The PHA production amount was 10.4 g/L, and the weight average molecular weight was $91\times10^4$. The results are shown in Table 1.

(Comparative Example 2) Production of PHA by KNK-005 ΔphaZ1,2,6 Strain

PHA was produced by the same method as in Example 1, using the KNK-005 ΔphaZ1,2,6 strain instead of the KNK-005 ΔphaZ1,2,6/pCUP2-PlacN17-glpK$_{Ec}$ strain, and the production amount and weight average molecular weight of the resultant PHA were measured. However, no kanamycin was added to the seed medium. The PHA production amount was 10.7 g/L, and the weight average molecular weight was $136\times10^4$. The results are shown in Table 1.

TABLE 1

| | Name of bacterial strain | PHA production amount (g/L) | Weight average molecular weight ($\times10^4$) |
|---|---|---|---|
| Example 1 | KNK-005 ΔphaZ1, 2, 6/ pCUP2-PlacN17-glpK$_{Ec}$ | 11.8 | 217 |
| Comparative Example 1 | KNK-005 | 10.4 | 91 |
| Comparative Example 2 | KNK-005 ΔphaZ1, 2, 6 | 10.7 | 136 |

As shown in Table 1, in Example 1, the glycerol kinase activity was enhanced by introduction of a gene encoding glycerol kinase derived from *E. coli*, so that the weight average molecular weight could be improved by about 1.6 times compared to Comparative Example 2. In the KNK-005 ΔphaZ1,2,6 strain of Comparative Example 2, which is a parent strain of Example 1, the weight average molecular weight was increased by about 1.5 times with respect to the KNK-005 strain of Comparative Example 1 due to disruption of the phaZ gene as a PHA degrading enzyme. However, as shown in Example 1, enhancement of the glycerol kinase activity by introduction of the gene encoding glycerol kinase derived from *E. coli* had an effect of further increasing the weight average molecular weight as compared with Comparative Example 2.

(Example 2) Production of PHA by KNK-005 REP-phaJ4b ΔphaZ1::Plac-phaC$_{Re}$ ΔZ,2,6/pCUP2-PlacN17-glpK$_{Ec}$ Strain PHA was produced by the same method as in Example 1, using the KNK-005 REP-phaJ4b ΔphaZ1::Plac-phaC$_{Re}$ ΔZ,2,6/pCUP2-PlacN17-glpK$_{Ec}$ strain obtained in Production Example 3 instead of the KNK-005 ΔphaZ1,2,6/pCUP2-PlacN17-glpK$_{Ec}$ strain, and the production amount and weight average molecular weight of the resultant PHA were measured. The PHA production amount was 11.2 g/L, and the weight average molecular weight was $160\times10^4$. The results are shown in Table 2.

(Example 3) Production of PHA by KNK-005 REP-phaJ4b ΔphaZ1::Plac-phaC$_{Re}$ ΔphaZ6::Plac-glpK$_{Ec}$ ΔZ,2 Strain PHA was produced by the same method as in Example 1, using the KNK-005 REP-phaJ4b ΔphaZ1::Plac-phaC$_{Re}$ ΔphaZ6::Plac-glpK$_{Ec}$ ΔZ2 strain obtained in Production Example 4 instead of the KNK-005 ΔphaZ1,2,6/pCUP2-PlacN17-glp$K_{Ec}$ strain, and the production amount and weight average molecular weight of the resultant PHA were measured. However, no kanamycin was added to the seed medium. The PHA production amount was 12.2 g/L, and the weight average molecular weight was 186×$10^4$. The results are shown in Table 2.

(Example 4) Production of PHA by KNK-005 REP-phaJ4b ΔphaZ1::Plac-pha$C_{Re}$ ΔphaZ6::PlacN17-glp$K_{Ec}$ ΔZ,2 Strain PHA was produced by the same method as in Example 1, using the KNK-005 REP-phaJ4b ΔphaZ1::Plac-pha$C_{Re}$ ΔphaZ6::PlacN17-glp$K_{Ec}$ ΔZ2 strain obtained in Production Example 5 instead of the KNK-005 ΔphaZ1,2,6/pCUP2-PlacN17-glp$K_{Ec}$ strain, and the production amount and weight average molecular weight of the resultant PHA were measured. However, no kanamycin was added to the seed medium. The PHA production amount was 11.9 g/L, and the weight average molecular weight was 195×$10^4$. The results are shown in Table 2.

(Example 5) Production of PHA by KNK-005 REP-phaJ4b PlacUV5-A2507 ΔphaZ1::Plac-pha$C_{Re}$ ΔZ,2,6 Strain PHA was produced by the same method as in Example 1, using the KNK-005 REP-phaJ4b PlacUV5-A2507 ΔphaZ1::Plac-pha$C_{Re}$ ΔZ,2,6 strain obtained in Production Example 6 instead of the KNK-005 ΔphaZ1,2,6/pCUP2-PlacN17-glp$K_{Ec}$ strain, and the production amount and weight average molecular weight of the resultant PHA were measured. However, no kanamycin was added to the seed medium. The PHA production amount was 7.6 g/L, and the weight average molecular weight was 186×$10^4$. The results are shown in Table 2.

(Example 6) Production of PHA by KNK-005 REP-phaJ4b ΔphaZ1::Plac-pha$C_{Re}$ ΔphaZ6::PlacUV5-A2507 ΔZ,2 Strain PHA was produced by the same method as in Example 1, using the KNK-005 REP-phaJ4b ΔphaZ1::Plac-pha$C_{Re}$ ΔphaZ6::PlacUV5-A2507 ΔZ,2 strain obtained in Production Example 7 instead of the KNK-005 ΔphaZ1,2,6/pCUP2-PlacN17-glp$K_{Ec}$ strain, and the production amount and weight average molecular weight of the resultant PHA were measured. However, no kanamycin was added to the seed medium. The PHA production amount was 10.8 g/L, and the weight average molecular weight was 177×$10^4$. The results are shown in Table 2.

(Comparative Example 3) Production of PHA by KNK-005 REP-phaJ4b ΔphaZ1::Plac-pha$C_{Re}$ ΔZ,2,6 Strain PHA was produced by the same method as in Example 1, using the KNK-005 REP-phaJ4b ΔphaZ1::Plac-pha$C_{Re}$ ΔZ,2,6 strain (see WO 2015/146195) instead of the KNK-005 ΔphaZ1,2,6/pCUP2-PlacN17-glp$K_{Ec}$ strain, and the production amount and weight average molecular weight of the resultant PHA were measured. However, no kanamycin was added to the seed medium. The PHA production amount was 10.0 g/L, and the weight average molecular weight was 117×$10^4$. The results are shown in Table 2.

TABLE 2

| | Name of bacterial strain | PHA production amount (g/L) | Weight average molecular weight (×$10^4$) |
|---|---|---|---|
| Example 2 | KNK-005 REP-phaJ4b ΔphaZ1::Plac-pha$C_{Re}$ ΔZ2, 6/pCUP2-PlacN17-glp$K_{Ec}$ | 11.2 | 160 |
| Example 3 | KNK-005 REP-phaJ4b ΔphaZ1::Plac-pha$C_{Re}$ ΔphaZ6::Plac-glp$K_{Ec}$ ΔZ2 | 12.2 | 186 |
| Example 4 | KNK-005 REP-phaJ4b ΔphaZ1::Plac-pha$C_{Re}$ ΔphaZ6::PlacN17-glp$K_{Ec}$ ΔZ2 | 11.9 | 195 |
| Example 5 | KNK-005 REP-phaJ4b PlacUV5-A2507 ΔphaZ1::Plac-pha$C_{Re}$ ΔZ2, 6 | 7.6 | 186 |
| Example 6 | KNK-005 REP-phaJ4b ΔphaZ1::Plac-pha$C_{Re}$ ΔphaZ6::PlacUV5-A2507 ΔZ2 | 10.8 | 177 |
| Comparative Example 3 | KNK-005 REP-phaJ4b ΔphaZ1::Plac-pha$C_{Re}$ ΔZ2, 6 | 10.0 | 117 |

As shown in Table 2, in Example 2, the glycerol kinase activity was enhanced by introduction of a gene encoding glycerol kinase derived from *E. coli* using plasmid, so that the weight average molecular weight could be improved by about 1.4 times compared to Comparative Example 3. In Examples 3 and 4, the glycerol kinase activity was enhanced by introduction of a gene encoding glycerol kinase derived from *E. coli* into a host genome, so that the weight average molecular weight could be increased by about 1.6 times and about 1.7 times, respectively, compared to Comparative Example 3. Example 3 and Example 4 differed in the expression regulatory sequence upstream of the gene encoding glycerol kinase derived from *E. coli*, but both had an effect of increasing the weight average molecular weight. In Example 5, the glycerol kinase activity was enhanced by inserting an expression regulatory sequence upstream of a gene encoding glycerol kinase present in a host genome, so that the weight average molecular weight could be increased by about 1.6 times compared to Comparative Example 3. In Example 6, the glycerol kinase activity was enhanced by inserting a copy of the gene encoding glycerol kinase present in a host genome into a different region on the genome, so that the weight average molecular weight could be increased by about 1.5 times compared to Comparative Example 3.

The invention claimed is:

1. A microorganism capable of producing a polyhydroxyalkanoate (PHA), comprising a gene encoding a PHA synthase derived from *Aeromonas caviae,* wherein at least a portion of a PHA degrading enzyme gene of the microorganism is altered by substitution, deletion, insertion, and/or addition of at least one nucleotide such that an activity of a PHA degrading enzyme encoded by the PHA degrading enzyme gene is eliminated or reduced as compared to an activity of the PHA degrading enzyme of a host of the microorganism, and a glycerol kinase activity of the microorganism is enhanced by introducing a gene encoding exogenous glycerol kinase as compared to a glycerol kinase activity of a host of the microorganism, wherein the gene encoding exogenous glycerol kinase is derived from *Escherichia coli.*

2. The microorganism according to claim 1, wherein the microorganism does not have an enhanced activity to uptake glycerol into cells as compared to a glycerol uptake activity of the host.

3. The microorganism according to claim 1, wherein the microorganism is a transformant of a microorganism belonging to genus *Cupriavidus.*

4. The microorganism according to claim 3, wherein the microorganism belonging to genus *Cupriavidus* is *Cupriavidus necator.*

5. A method for producing PHA, comprising culturing the microorganism according to claim 1.

6. The method according to claim 5, wherein in the culturing, the microorganism is cultured in the presence of a carbon source comprising glycerol and/or a compound having a glycerol skeleton.

7. The method according to claim 5, wherein the PHA is a copolymerized PHA comprising a structural unit derived from 3-hydroxybutyric acid.

8. The method according to claim 7, wherein the copolymerized PHA comprises a structural unit derived from 3-hydroxybutyric acid and 3-hydroxyhexanoic acid.

9. The microorganism according to claim 1, wherein the activity of the PHA degrading enzyme of the microorganism is reduced to 20% or lower of an activity of the PHA degrading enzyme of the host which does not have the substitution, deletion, insertion, and/or addition.

10. The microorganism according to claim 1, wherein the activity of the PHA degrading enzyme of the microorganism is eliminated by the substitution, deletion, insertion, and/or addition.

11. The microorganism according to claim 1, which is capable of producing a copolymerized PHA comprising a structural unit derived from 3-hydroxybutyric acid.

12. The microorganism according to claim 1, wherein the PHA produced by the microorganism has a weight average molecular weight of from 300,000 to 4,000,000.

13. The microorganism according to claim 1, wherein the PHA produced by the microorganism has a weight average molecular weight of $160\times10^4$ or higher.

14. The microorganism according to claim 1, wherein the PHA degrading enzyme gene is a phaZ gene.

* * * * *

SEQUENCE LISTING

```
<160> NUMBER OF SEQ ID NOS: 61

<210> SEQ ID NO 1
<211> LENGTH: 594
<212> TYPE: PRT
<213> ORGANISM: Aeromonas caviae
```

```
<400> SEQUENCE: 1

Met Ser Gln Pro Ser Tyr Gly Pro Leu Phe Glu Ala Leu Ala His Tyr
1               5                   10                  15

Asn Asp Lys Leu Leu Ala Met Ala Lys Ala Gln Thr Glu Arg Thr Ala
            20                  25                  30

Gln Ala Leu Leu Gln Thr Asn Leu Asp Asp Leu Gly Gln Val Leu Glu
        35                  40                  45

Gln Gly Ser Gln Gln Pro Trp Gln Leu Ile Gln Ala Gln Met Asn Trp
    50                  55                  60

Trp Gln Asp Gln Leu Lys Leu Met Gln His Thr Leu Leu Lys Ser Ala
65                  70                  75                  80

Gly Gln Pro Ser Glu Pro Val Ile Thr Pro Glu Arg Ser Asp Arg Arg
                85                  90                  95

Phe Lys Ala Glu Ala Trp Ser Glu Gln Pro Ile Tyr Asp Tyr Leu Lys
            100                 105                 110

Gln Ser Tyr Leu Leu Thr Ala Arg His Leu Leu Ala Ser Val Asp Ala
        115                 120                 125

Leu Glu Gly Val Pro Gln Lys Ser Arg Glu Arg Leu Arg Phe Phe Thr
    130                 135                 140

Arg Gln Tyr Val Asn Ala Met Ala Pro Ser Asn Phe Leu Ala Thr Asn
145                 150                 155                 160

Pro Glu Leu Leu Lys Leu Thr Leu Glu Ser Asp Gly Gln Asn Leu Val
                165                 170                 175

Arg Gly Leu Ala Leu Leu Ala Glu Asp Leu Glu Arg Ser Ala Asp Gln
            180                 185                 190

Leu Asn Ile Arg Leu Thr Asp Glu Ser Ala Phe Glu Leu Gly Arg Asp
        195                 200                 205

Leu Ala Leu Thr Pro Gly Arg Val Val Gln Arg Thr Glu Leu Tyr Glu
    210                 215                 220

Leu Ile Gln Tyr Ser Pro Thr Thr Glu Thr Val Gly Lys Thr Pro Val
225                 230                 235                 240

Leu Ile Val Pro Pro Phe Ile Asn Lys Tyr Tyr Ile Met Asp Met Arg
                245                 250                 255

Pro Gln Asn Ser Leu Val Ala Trp Leu Val Ala Gln Gly Gln Thr Val
            260                 265                 270

Phe Met Ile Ser Trp Arg Asn Pro Gly Val Ala Gln Ala Gln Ile Asp
        275                 280                 285

Leu Asp Asp Tyr Val Val Asp Gly Val Ile Ala Ala Leu Asp Gly Val
    290                 295                 300

Glu Ala Ala Thr Gly Glu Arg Glu Val His Gly Ile Gly Tyr Cys Ile
305                 310                 315                 320

Gly Gly Thr Ala Leu Ser Leu Ala Met Gly Trp Leu Ala Ala Arg Arg
                325                 330                 335

Gln Lys Gln Arg Val Arg Thr Ala Thr Leu Phe Thr Thr Leu Leu Asp
            340                 345                 350

Phe Ser Gln Pro Gly Glu Leu Gly Ile Phe Ile His Glu Pro Ile Ile
        355                 360                 365

Ala Ala Leu Glu Ala Gln Asn Glu Ala Lys Gly Ile Met Asp Gly Arg
    370                 375                 380

Gln Leu Ala Val Ser Phe Ser Leu Leu Arg Glu Asn Ser Leu Tyr Trp
385                 390                 395                 400

Asn Tyr Tyr Ile Asp Ser Tyr Leu Lys Gly Gln Ser Pro Val Ala Phe
                405                 410                 415
```

-continued

```
Asp Leu Leu His Trp Asn Ser Asp Ser Thr Asn Val Ala Gly Lys Thr
            420                 425                 430

His Asn Ser Leu Leu Arg Arg Leu Tyr Leu Glu Asn Gln Leu Val Lys
        435                 440                 445

Gly Glu Leu Lys Ile Arg Asn Thr Arg Ile Asp Leu Gly Lys Val Lys
    450                 455                 460

Thr Pro Val Leu Leu Val Ser Ala Val Asp Asp His Ile Ala Leu Trp
465                 470                 475                 480

Gln Gly Thr Trp Gln Gly Met Lys Leu Phe Gly Gly Glu Gln Arg Phe
                485                 490                 495

Leu Leu Ala Glu Ser Gly His Ile Ala Gly Ile Ile Asn Pro Pro Ala
            500                 505                 510

Ala Asn Lys Tyr Gly Phe Trp His Asn Gly Ala Glu Ala Glu Ser Pro
        515                 520                 525

Glu Ser Trp Leu Ala Gly Ala Thr His Gln Gly Gly Ser Trp Trp Pro
    530                 535                 540

Glu Met Met Gly Phe Ile Gln Asn Arg Asp Glu Gly Ser Glu Pro Val
545                 550                 555                 560

Pro Ala Arg Val Pro Glu Glu Gly Leu Ala Pro Ala Pro Gly His Tyr
                565                 570                 575

Val Lys Val Arg Leu Asn Pro Val Phe Ala Cys Pro Thr Glu Glu Asp
            580                 585                 590

Ala Ala


<210> SEQ ID NO 2
<211> LENGTH: 1785
<212> TYPE: DNA
<213> ORGANISM: Aeromonas caviae

<400> SEQUENCE: 2

atgagccaac catcttatgg cccgctgttc gaggccctgg cccactacaa tgacaagctg      60

ctggccatgg ccaaggccca gacagagcgc accgcccagg cgctgctgca gaccaatctg     120

gacgatctgg gccaggtgct ggagcagggc agccagcaac cctggcagct gatccaggcc     180

cagatgaact ggtggcagga tcagctcaag ctgatgcagc acaccctgct caaaagcgca     240

ggccagccga gcgagccggt gatcaccccg gagcgcagcg atcgccgctt caaggccgag     300

gcctggagcg aacaacccat ctatgactac ctcaagcagt cctacctgct caccgccagg     360

cacctgctgg cctcggtgga tgccctggag ggcgtccccc agaagagccg ggagcggctg     420

cgtttcttca cccgccagta cgtcaacgcc atggccccca gcaacttcct ggccaccaac     480

cccgagctgc tcaagctgac cctggagtcc gacggccaga acctggtgcg cggactggcc     540

ctcttggccg aggatctgga gcgcagcgcc gatcagctca acatccgcct gaccgacgaa     600

tccgccttcg agctcgggcg ggatctggcc ctgaccccgg gccgggtggt gcagcgcacc     660

gagctctatg agctcattca gtacagcccg actaccgaga cggtgggcaa gacacctgtg     720

ctgatagtgc cgcccttcat caacaagtac tacatcatgg acatgcggcc ccagaactcc     780

ctggtcgcct ggctggtcgc ccagggccag acggtattca tgatctcctg gcgcaacccg     840

ggcgtggccc aggcccaaat cgatctcgac gactacgtgg tggatggcgt catcgccgcc     900

ctggacggcg tggaggcggc caccggcgag cgggaggtgc acggcatcgg ctactgcatc     960

ggcggcaccg ccctgtcgct cgccatgggc tggctggcgg cgcggcgcca gaagcagcgg    1020

gtgcgcaccg ccaccctgtt cactaccctg ctggacttct cccagcccgg ggagcttggc    1080
```

-continued atcttcatcc acgagcccat catagcggcg ctcgaggcgc aaaatgaggc caagggcatc 1140
atggacgggc gccagctggc ggtctccttc agcctgctgc gggagaacag cctctactgg 1200
aactactaca tcgacagcta cctcaagggt cagagcccgg tggccttcga tctgctgcac 1260
tggaacagcg acagcaccaa tgtggcgggc aagacccaca acagcctgct gcgccgtctc 1320
tacctggaga accagctggt gaagggggag ctcaagatcc gcaacacccg catcgatctc 1380
ggcaaggtga agacccctgt gctgctggtg tcggcggtgg acgatcacat cgccctctgg 1440
cagggcacct ggcagggcat gaagctgttt ggcggggagc agcgcttcct cctggcggag 1500
tccggccaca tcgccggcat catcaacccg ccggccgcca acaagtacgg cttctggcac 1560
aacggggccg aggccgagag cccggagagc tggctggcag gggcgacgca ccagggcggc 1620
tcctggtggc ccgagatgat gggctttatc cagaaccgtg acgaagggtc agagcccgtc 1680
cccgcgcggg tcccggagga agggctggcc cccgcccccg gccactatgt caaggtgcgg 1740
ctcaaccccg tgtttgcctg cccaacagag gaggacgccg catga 1785

<210> SEQ ID NO 3
<211> LENGTH: 1785
<212> TYPE: DNA
<213> ORGANISM: Artificial Sequence
<220> FEATURE:
<223> OTHER INFORMATION: Artificially mutated gene derived from Aeromonas caviae

<400> SEQUENCE: 3
atgagccaac catcttatgg cccgctgttc gaggccctgg cccactacaa tgacaagctg 60
ctggccatgg ccaaggccca gacagagcgc accgcccagg cgctgctgca gaccaatctg 120
gacgatctgg gccaggtgct ggagcagggc agccagcaac cctggcagct gatccaggcc 180
cagatgaact ggtggcagga tcagctcaag ctgatgcagc acaccctgct caaaagcgca 240
ggccagccga gcgagccggt gatcaccccg gagcgcagcg atcgccgctt caaggccgag 300
gcctggagcg aacaacccat ctatgactac ctcaagcagt cctacctgct caccgccagg 360
cacctgctgg cctcggtgga tgccctggag ggcgtccccc agaagagccg ggagcggctg 420
cgtttcttca cccgccagta cgtcagcgcc atggccccca gcaacttcct ggccaccaac 480
cccgagctgc tcaagctgac cctggagtcc ggcggccaga acctggtgcg cggactggcc 540
ctcttggccg aggatctgga gcgcagcgcc gatcagctca acatccgcct gaccgacgaa 600
tccgccttcg agctcgggcg ggatctggcc ctgacccccgg gccgggtggt gcagcgcacc 660
gagctctatg agctcattca gtacagcccg actaccgaga cggtgggcaa gacacctgtg 720
ctgatagtgc cgcccttcat caacaagtac tacatcatgg acatgcggcc ccagaactcc 780
ctggtcgcct ggctggtcgc ccagggccag acggtattca tgatctcctg gcgcaacccg 840
ggcgtggccc aggcccaaat cgatctcgac gactacgtgg tggatggcgt catcgccgcc 900
ctggacggcg tggaggcggc caccggcgag cgggaggtgc acggcatcgg ctactgcatc 960
ggcggcaccg ccctgtcgct cgccatgggc tggctggcgg cgcggcgcca gaagcagcgg 1020
gtgcgcaccg ccaccctgtt cactaccctg ctggacttct cccagcccgg ggagcttggc 1080
atcttcatcc acgagcccat catagcggcg ctcgaggcgc aaaatgaggc caagggcatc 1140
atggacgggc gccagctggc ggtctccttc agcctgctgc gggagaacag cctctactgg 1200
aactactaca tcgacagcta cctcaagggt cagagcccgg tggccttcga tctgctgcac 1260
tggaacagcg acagcaccaa tgtggcgggc aagacccaca acagcctgct gcgccgtctc 1320

-continued

```
tacctggaga accagctggt gaagggggag ctcaagatcc gcaacacccg catcgatctc   1380

ggcaaggtga agacccctgt gctgctggtg tcggcggtgg acgatcacat cgccctctgg   1440

cagggcacct ggcagggcat gaagctgttt ggcggggagc agcgcttcct cctggcggag   1500

tccggccaca tcgccggcat catcaacccg ccggccgcca acaagtacgg cttctggcac   1560

aacggggccg aggccgagag cccggagagc tggctggcag gggcgacgca ccagggcggc   1620

tcctggtggc ccgagatgat gggctttatc cagaaccgtg acgaagggtc agagcccgtc   1680

cccgcgcggg tcccggagga agggctggcc cccgcccccg gccactatgt caaggtgcgg   1740

ctcaaccccg tgtttgcctg cccaacagag gaggacgccg catga                   1785
```

```
<210> SEQ ID NO 4
<211> LENGTH: 123
<212> TYPE: DNA
<213> ORGANISM: Escherichia coli

<400> SEQUENCE: 4

gcgcaacgca attaatgtga gttagctcac tcattaggca ccccaggctt tacactttat     60

gcttccggct cgtatgttgt gtggaattgt gagcggataa caatttcaca caggaaacaa    120

ttg                                                                  123


<210> SEQ ID NO 5
<211> LENGTH: 232
<212> TYPE: DNA
<213> ORGANISM: Escherichia coli

<400> SEQUENCE: 5

tgcttctggc gtcaggcagc catcggaagc tgtggtatgg ctgtgcaggt cgtaaatcac     60

tgcataattc gtgtcgctca aggcgcactc ccgttctgga taatgttttt tgcgccgaca    120

tcataacggt tctggcaaat attctgaaat gagctgttga caattaatca tcgaactagt    180

taactagtac gcaagttcac agcggataac aatttcacac aggaaacaat tg            232


<210> SEQ ID NO 6
<211> LENGTH: 123
<212> TYPE: DNA
<213> ORGANISM: Artificial Sequence
<220> FEATURE:
<223> OTHER INFORMATION: Artificially mutated promoter derived from
      Escherichia coli

<400> SEQUENCE: 6

gcgcaacgca attaatgtga gttagctcac tcattaggca ccccaggctt tacactttat     60

gcttccggct cgtataatgt gtggaattgt gagcggataa caatttcaca caggaaacaa    120

ttg                                                                  123


<210> SEQ ID NO 7
<211> LENGTH: 120
<212> TYPE: DNA
<213> ORGANISM: Artificial Sequence
<220> FEATURE:
<223> OTHER INFORMATION: Artificially mutated promoter derived from
      Escherichia coli

<400> SEQUENCE: 7

gcgcaacgca attaatgtga gttagctcac tcattaggca ccccaggctt tacacatgct     60

tccggctcgt atgttgtgtg gaattgtgag cggataacaa tttcacacag gaaacaattg    120
```

<210> SEQ ID NO 8
<211> LENGTH: 121
<212> TYPE: DNA
<213> ORGANISM: Artificial Sequence
<220> FEATURE:
<223> OTHER INFORMATION: Artificially mutated promoter derived from
      Escherichia coli

<400> SEQUENCE: 8
gcgcaacgca attaatgtga gttagctcac tcattaggca ccccaggctt tacactatgc     60
ttccggctcg tatgttgtgt ggaattgtga gcggataaca atttcacaca ggaaacaatt    120
g                                                                    121

<210> SEQ ID NO 9
<211> LENGTH: 122
<212> TYPE: DNA
<213> ORGANISM: Artificial Sequence
<220> FEATURE:
<223> OTHER INFORMATION: Artificially mutated promoter derived from
      Escherichia coli

<400> SEQUENCE: 9
gcgcaacgca attaatgtga gttagctcac tcattaggca ccccaggctt tacacttatg     60
cttccggctc gtatgttgtg tggaattgtg agcggataac aatttcacac aggaaacaat    120
tg                                                                   122

<210> SEQ ID NO 10
<211> LENGTH: 124
<212> TYPE: DNA
<213> ORGANISM: Artificial Sequence
<220> FEATURE:
<223> OTHER INFORMATION: Artificially mutated promoter derived from
      Escherichia coli

<400> SEQUENCE: 10
gcgcaacgca attaatgtga gttagctcac tcattaggca ccccaggctt tacacccttta     60 tgcttccggc tcgtatgttg tgtggaattg tgagcggata acaatttcac acaggaaaca    120
attg                                                                 124

<210> SEQ ID NO 11
<211> LENGTH: 125
<212> TYPE: DNA
<213> ORGANISM: Artificial Sequence
<220> FEATURE:
<223> OTHER INFORMATION: Artificially mutated promoter derived from
      Escherichia coli

<400> SEQUENCE: 11
gcgcaacgca attaatgtga gttagctcac tcattaggca ccccaggctt tacacccttt     60
atgcttccgg ctcgtatgtt gtgtggaatt gtgagcggat aacaatttca cacaggaaac    120
aattg                                                                125

<210> SEQ ID NO 12
<211> LENGTH: 126
<212> TYPE: DNA
<213> ORGANISM: Artificial Sequence
<220> FEATURE:
<223> OTHER INFORMATION: Artificially mutated promoter derived from
      Escherichia coli

<400> SEQUENCE: 12

```
gcgcaacgca attaatgtga gttagctcac tcattaggca ccccaggctt tacacccttt    60

tatgcttccg gctcgtatgt tgtgtggaat tgtgagcgga taacaatttc acacaggaaa   120

caattg                                                              126

<210> SEQ ID NO 13
<211> LENGTH: 235
<212> TYPE: DNA
<213> ORGANISM: Artificial Sequence
<220> FEATURE:
<223> OTHER INFORMATION: artificial promoter

<400> SEQUENCE: 13

caattgtgct tctggcgtca ggcagccatc ggaagctgtg gtatggctgt gcaggtcgta    60

aatcactgca taattcgtgt cgctcaaggc gcactcccgt tctggataat gttttttgcg   120

ccgacatcat aacggttctg gcaaatattc tgaaatgagc tgttgacaat taatcatcgg   180

ctcgtataat gtgtggaatt gtgagcggat aacaatttca cacaggaaac aattg        235

<210> SEQ ID NO 14
<211> LENGTH: 236
<212> TYPE: DNA
<213> ORGANISM: Artificial Sequence
<220> FEATURE:
<223> OTHER INFORMATION: artificial promoter

<400> SEQUENCE: 14

caattgtgct tctggcgtca ggcagccatc ggaagctgtg gtatggctgt gcaggtcgta    60

aatcactgca taattcgtgt cgctcaaggc gcactcccgt tctggataat gttttttgcg   120

ccgacatcat aacggttctg gcaaatattc tgaaatgagc tgttgacaat taatcatcga   180

actagtttaa tgtgtggaat tgtgagcgga taacaatttc acacaggaaa caattg       236

<210> SEQ ID NO 15
<211> LENGTH: 237
<212> TYPE: DNA
<213> ORGANISM: Artificial Sequence
<220> FEATURE:
<223> OTHER INFORMATION: artificial promoter

<400> SEQUENCE: 15

caattgtgct tctggcgtca ggcagccatc ggaagctgtg gtatggctgt gcaggtcgta    60

aatcactgca taattcgtgt cgctcaaggc gcactcccgt tctggataat gttttttgcg   120

ccgacatcat aacggttctg gcaaatattc tgaaatgagc tgttgacaat taatcatcgc   180

ggctcgtata atgtgtggaa ttgtgagcgg ataacaattt cacacaggaa acaattg      237

<210> SEQ ID NO 16
<211> LENGTH: 236
<212> TYPE: DNA
<213> ORGANISM: Artificial Sequence
<220> FEATURE:
<223> OTHER INFORMATION: artificial promoter

<400> SEQUENCE: 16

caattgtgct tctggcgtca ggcagccatc ggaagctgtg gtatggctgt gcaggtcgta    60

aatcactgca taattcgtgt cgctcaaggc gcactcccgt tctggataat gttttttgcg   120

ccgacatcat aacggttctg gcaaatattc tgaaatgagc tgttgacaat taatcatccg   180

gctcgtataa tgtgtggaat tgtgagcgga taacaatttc acacaggaaa caattg       236
```

<210> SEQ ID NO 17
<211> LENGTH: 818
<212> TYPE: DNA
<213> ORGANISM: Cupriavidus necator

<400> SEQUENCE: 17
cccgggcaag taccttgccg acatctatgc gctggcgcgc acgcgcctgg cgcgcgccgg 60
ctgtaccgag gtctacggcg gcgacgcctg caccgtggcc gacgccggtc gcttctactc 120
ctatcggcgc gatggcgtga ccggccgcat ggccagcctg gtctggctgg cggactgagc 180
ccgccgctgc ctcactcgtc cttgcccctg gccgcctgcg cgcgctcggc ttcagccttg 240
cgtcggcggc ggccgggcgt gcccatgatg tagagcacca gcgccaccgg cgccatgcca 300
tacatcagga aggtggcaac gcctgccacc acgttgtgct cggtgatcgc catcatcagc 360
gccacgtaga gccagccaat ggccacgatg tacatcaaaa attcatcctt ctcgcctatg 420
ctctggggcc tcggcagatg cgagcgctgc ataccgtccg gtaggtcggg aagcgtgcag 480
tgccgaggcg gattcccgca ttgacagcgc gtgcgttgca aggcaacaat ggactcaaat 540
gtctcggaat cgctgacgat tcccaggttt ctccggcaag catagcgcat ggcgtctcca 600
tgcgagaatg tcgcgcttgc cggataaaag gggagccgct atcggaatgg acgcaagcca 660
cggccgcagc aggtgcggtc gagggcttcc agccagttcc agggcagatg tgccggcaga 720
ccctcccgct ttgggggagg cgcaagccgg gtccattcgg atagcatctc cccatgcaaa 780
gtgccggcca gggcaatgcc cggagccggt tcgaatag 818

<210> SEQ ID NO 18
<211> LENGTH: 817
<212> TYPE: DNA
<213> ORGANISM: Artificial Sequence
<220> FEATURE:
<223> OTHER INFORMATION: Artificially mutated promoter derived from
Cupriavidus necator

<400> SEQUENCE: 18
cccgggcaag taccttgccg acatctatgc gctggcgcgc acgcgcctgg cgcgcgccgg 60
ctgtaccgag gtctacggcg gcgacgcctg caccgtggcc gacgccggtc gcttctactc 120
ctatcggcgc gatggcgtga ccggccgcat ggccagcctg gtctggctgg cggactgagc 180
ccgccgctgc ctcactcgtc cttgcccctg gccgcctgcg cgcgctcggc ttcagccttg 240
cgtcggcggc ggccgggcgt gcccatgatg tagagcacca gcgccaccgg cgccatgcca 300
tacatcagga aggtggcaac gcctgccacc acgttgtgct cggtgatcgc catcatcagc 360
gccacgtaga gccagccaat ggccacgatg tacatcaaaa attcatcctt ctcgcctatg 420
ctctggggcc tcggcagatg cgagcgctgc ataccgtccg gtaggtcggg aagcgtgcag 480
tgccgaggcg gattcccgca ttgacagcgc gtgcttgcaa ggcaacaatg gactcaaatg 540
tctcggaatc gctgacgatt cccaggtttc tccggcaagc atagcgcatg gcgtctccat 600
gcgagaatgt cgcgcttgcc ggataaaagg ggagccgcta tcggaatgga cgcaagccac 660
ggccgcagca ggtgcggtcg agggcttcca gccagttcca gggcagatgt gccggcagac 720
cctcccgctt tgggggaggc gcaagccggg tccattcgga tagcatctcc ccatgcaaag 780
tgccggccag ggcaatgccc ggagccggtt cgaatag 817

<210> SEQ ID NO 19
<211> LENGTH: 268
<212> TYPE: DNA
<213> ORGANISM: Cupriavidus necator

<400> SEQUENCE: 19
catggccctc gccggagcgc cccggagtgg cgtcacagcc gctcccgtgt atcgccagca 60
acgttgtttg tgcattgcac aaaatccact tgacattgga tctggcgccc ctaaaatagg 120
aattgttgcg gcgcaccaaa taagaaatgc gccttgaccc acccacacgc ctgggctggc 180
cgaatcgggc acaacaccgt cacggccctg acatctaggc ggcttaattt gctagacctt 240
gaagttcacc actggagacc agcaattg 268

<210> SEQ ID NO 20
<211> LENGTH: 24
<212> TYPE: DNA
<213> ORGANISM: Cupriavidus necator

<400> SEQUENCE: 20
cacgtgcaga gagacaatca aatc 24

<210> SEQ ID NO 21
<211> LENGTH: 24
<212> TYPE: DNA
<213> ORGANISM: Artificial Sequence
<220> FEATURE:
<223> OTHER INFORMATION: Artificially mutated SD sequence derived from Cupriavidus necator

<400> SEQUENCE: 21
cacgtgctct ctctcaatca aatc 24

<210> SEQ ID NO 22
<211> LENGTH: 670
<212> TYPE: DNA
<213> ORGANISM: Cupriavidus necator

<400> SEQUENCE: 22
tgagtagtga gccgcgtgga ttctgcgcca tgcggttgtt cccgaacggt cgttctaaaa 60
aatttagcac gaccgttcac aaaatttcga ttcgcggata atatagcttt tgacgggctg 120
gaaagatcat gaaggtgctc gacctgcgct gcgcgcatga ccatggtttc gagggctggt 180
ttgcctcgga agaagatgcg cagtcgcaaa tctcgcgtga cctcgtccaa tgcccggtct 240
gtggcgacca cgccgtgacg cggctgccca gcgcgccgcg cctgaacctg tcgggcgcga 300
ccgcgcgcga aggcagcgcc aggccggcgc agccggctgc cgcaccggag acactgcaag 360
cgctctatat gaaggcagtg aagcaggtgc tggcacagac cgaggatgtt ggcgatcgct 420
ttgccgaaga ggcaaggcgc atgcactatg acgaggcgcc ggaacgcggc attcgcggtt 480
cggcctcggc ggaggaggtg caggcgctgg ccgaagaggg catcgagact ttcccgctcg 540
tggtgccgga tgcgctgaag cagacggctc actgaattgc gtcttgtgcc cgtttgctgt 600
cggcgcttga cgtgcaggca gaacaaaccg ccggcggccc cacgccaagc cggcaccact 660
ggagacgggc 670

<210> SEQ ID NO 23
<211> LENGTH: 385
<212> TYPE: DNA
<213> ORGANISM: Aeromonas caviae

<400> SEQUENCE: 23
cgatctggac cggggtgctg gcctgggcca cgccggcgag ggccagcgcg gagcaaccga 60
gcagcagggc gagaggtttc atcgggattc cttggcagtc tgaatgacgt gccagcctat 120

-continued

```
cagcgcggcg ccggtgcggc gagggcgcgc cggacccagt gcgtcacctc tcgtctgatc    180

cgcctccctc gacgggcgtc gctgacaaaa aaattcaaac agaaattaac atttatgtca    240

tttacaccaa accgcatttg gttgcagaat gctcaaacgt gtgtttgaac agagcaagca    300

acacgtaaac agggatgaca tgcagtaccc gtaagaaggg ccgattggcc cagatctcgc    360

ctcgggtgtg ggtgaaggag agcac                                          385
```

```
<210> SEQ ID NO 24
<211> LENGTH: 362
<212> TYPE: PRT
<213> ORGANISM: Cupriavidus necator

<400> SEQUENCE: 24

Met Thr Lys Ser Phe Ala Ala Asp Trp His Ala Gln Ile Arg Arg Leu
1               5                   10                  15

Ser Arg Ala Gln Ala Arg Thr Glu Ala Gln Val Lys Ser Trp Leu Asp
            20                  25                  30

Arg Val Asp Ser Leu Asn Pro Leu Thr Pro Ala Arg Pro Asp Arg Pro
        35                  40                  45

Pro Gly Lys Val Arg Pro Ala Arg Pro Ala Pro Ala Pro Gly Ser Leu
    50                  55                  60

Pro Gly Thr Trp Gln Ala His Arg Leu Arg Leu Ala Pro Leu Pro Gly
65                  70                  75                  80

Glu Leu Val Pro Gln Leu Ser Tyr His Leu Tyr Ile Pro Ser Lys Ala
                85                  90                  95

His Arg Gly Pro Leu Pro Val Val Val Val Leu His Gly Cys Arg Gln
            100                 105                 110

Thr Pro Asp Asp Leu Ser Ala Gly Thr Arg Met Asn Ala Leu Ala Glu
        115                 120                 125

Arg Glu Gly Phe Ile Val Ala Tyr Pro Gln Gln Pro Leu Arg Arg Gln
    130                 135                 140

Val Gln Arg Cys Trp Gln Trp Phe Asp Leu Gly Ala Ala Glu Gly Gly
145                 150                 155                 160

Arg Glu Ala Gln Ala Val Ala Ala Leu Ile Asp Ala Leu Ala Ala Arg
                165                 170                 175

His Asp Val Arg Glu Arg Glu Ile Tyr Leu Ala Gly Met Ser Ala Gly
            180                 185                 190

Ala Ala Met Ala Ala Val Val Ala Leu Arg Tyr Pro Gly Lys Val Ala
        195                 200                 205

Ala Ala Ala Leu His Ser Gly Val Val Ile Gly Ala Ala Asp Asn Pro
    210                 215                 220

Arg Ala Gly Leu Arg Ala Met Gln Gln Gly Ser Ala Ala Asp Pro Ser
225                 230                 235                 240

Trp Leu Leu Asp Ala Ala Gly Val Thr Pro Gly Gly Pro Glu Met Pro
                245                 250                 255

Ala Leu Val Ile His Gly Leu Ala Asp Asp Ala Val His Pro Val Asn
            260                 265                 270

Gly Arg Leu Leu Ala Arg Gln Phe Leu Ala Tyr Asn Gly Leu Glu Asp
        275                 280                 285

Arg Leu Ala Gly Ala Pro Ala Gln Ser Gly Pro Glu Asp Glu Ala Pro
    290                 295                 300

Gly Arg Ser His Glu Tyr Arg Phe Gly Arg Trp Arg Arg Asp Leu Val
305                 310                 315                 320
```

-continued

Thr Leu Val Glu Val Glu Gly Leu Gly His Ala Trp Ser Gly Gly Asp
325 330 335

Ala Ser Tyr Gly Tyr His Ser Asp Ile Gly Pro Asp Ala Ser Thr Met
340 345 350

Met Trp Gln Phe Phe Ser Gln His Arg Arg
355 360

<210> SEQ ID NO 25
<211> LENGTH: 1089
<212> TYPE: DNA
<213> ORGANISM: Cupriavidus necator

<400> SEQUENCE: 25
atgaccaaaa gctttgccgc tgactggcac gcgcagatcc ggcgactgag ccgtgcgcaa 60
gcccgcacgg aagcccaggt gaagtcctgg ctggaccgcg tggattcgct taatccgctc 120
acgccggctc ggcctgaccg cccgccgggc aaggtccggc ccgcccggcc agcacccgcg 180
ccgggttccc tgcccggtac ctggcaggcg cacaggctgc gcctggcgcc gctgccgggc 240
gaactggtgc cgcaactctc gtatcacctc tacataccgt ccaaggccca tcgcggcccg 300
ttgccggtgg tggtggtgct gcatggctgt cgccagacgc cggatgacct gtcggccggc 360
acccgcatga atgcgctggc cgagcgcgag ggatttatcg tggcctaccc gcaacagccc 420
ttgcggcgcc aggtgcagcg ctgctggcag tggttcgacc tgggcgccgc tgagggcgga 480
cgcgaggcgc aggcggtggc cgcgctgatc gatgcgctgg ctgcgcgcca cgacgtgcgc 540
gagcgcgaga tctacctggc cggcatgtcc gccggcgcgg ccatggccgc ggtggtggcg 600
ttgcgctacc cgggcaaggt ggcggccgcg gcgctgcatt ccggcgtggt catcggcgcc 660
gccgacaacc cgcgcgccgg cctgcgggcc atgcagcaag gctcggcggc cgatccgtca 720
tggctgctgg atgccgccgg cgtgacgccg ggcggtcccg agatgcccgc gctggtgatc 780
cacggcctgg ccgacgacgc ggtccatccg gtcaatggcc gtctgctggc gcggcagttc 840
ctggcttaca acggcctgga agaccggctc gccggtgcgc ccgcgcagtc cggcccggag 900
gacgaagcgc cgggccggtc tcatgaatac cgcttcggcc gctggcgccg cgacctggtc 960
acgctggtgg aagtggaggg cttgggccac gcctggagcg gcggcgatgc cagctatggc 1020
taccacagcg atatcggccc ggatgccagc acgatgatgt ggcagttctt cagccagcac 1080
cgccgttga 1089

<210> SEQ ID NO 26
<211> LENGTH: 419
<212> TYPE: PRT
<213> ORGANISM: Cupriavidus necator

<400> SEQUENCE: 26

Met Leu Tyr Gln Leu His Glu Phe Gln Arg Ser Ile Leu His Pro Leu
1 5 10 15

Thr Ala Trp Ala Gln Ala Thr Ala Lys Thr Phe Thr Asn Pro Leu Ser
20 25 30

Pro Leu Ser Leu Val Pro Gly Ala Pro Arg Leu Ala Ala Gly Tyr Glu
35 40 45

Leu Leu Tyr Arg Leu Gly Lys Glu Tyr Glu Lys Pro Ala Phe Asp Ile
50 55 60

Lys Ser Val Arg Ser Asn Gly Arg Asp Ile Pro Ile Val Glu Gln Thr
65 70 75 80

Val Leu Glu Lys Pro Phe Cys Lys Leu Val Arg Phe Lys Arg Tyr Ala

-continued

```
                85                  90                  95

Asp Asp Pro Glu Thr Ile Lys Leu Leu Lys Asp Glu Pro Val Val Leu
            100                 105                 110

Val Ala Ala Pro Leu Ser Gly His His Ala Thr Leu Leu Arg Asp Thr
        115                 120                 125

Val Arg Thr Leu Leu Gln Asp His Lys Val Tyr Val Thr Asp Trp Ile
    130                 135                 140

Asp Ala Arg Met Val Pro Val Glu Glu Gly Ala Phe His Leu Ser Asp
145                 150                 155                 160

Tyr Ile Tyr Tyr Ile Gln Glu Phe Ile Arg His Ile Gly Ala Glu Asn
                165                 170                 175

Leu His Val Ile Ser Val Cys Gln Pro Thr Val Pro Val Leu Ala Ala
            180                 185                 190

Ile Ser Leu Met Ala Ser Ala Gly Glu Lys Thr Pro Arg Thr Met Thr
        195                 200                 205

Met Met Gly Gly Pro Ile Asp Ala Arg Lys Ser Pro Thr Ala Val Asn
    210                 215                 220

Ser Leu Ala Thr Asn Lys Ser Phe Glu Trp Phe Glu Asn Asn Val Ile
225                 230                 235                 240

Tyr Thr Val Pro Ala Asn Tyr Pro Gly His Gly Arg Arg Val Tyr Pro
                245                 250                 255

Gly Phe Leu Gln His Ala Gly Phe Val Ala Met Asn Pro Asp Arg His
            260                 265                 270

Leu Ser Ser His Tyr Asp Phe Tyr Leu Ser Leu Val Glu Gly Asp Ala
        275                 280                 285

Asp Asp Ala Glu Ala His Val Arg Phe Tyr Asp Glu Tyr Asn Ala Val
    290                 295                 300

Leu Asp Met Ala Ala Glu Tyr Tyr Leu Asp Thr Ile Arg Glu Val Phe
305                 310                 315                 320

Gln Glu Phe Arg Leu Ala Asn Gly Thr Trp Ala Ile Asp Gly Asn Pro
                325                 330                 335

Val Arg Pro Gln Asp Ile Lys Ser Thr Ala Leu Met Thr Val Glu Gly
            340                 345                 350

Glu Leu Asp Asp Ile Ser Gly Ala Gly Gln Thr Ala Ala Ala His Asp
        355                 360                 365

Leu Cys Ala Gly Ile Pro Lys Ile Arg Lys Gln His Leu Asn Ala Ala
    370                 375                 380

His Cys Gly His Tyr Gly Ile Phe Ser Gly Arg Arg Trp Arg Glu Glu
385                 390                 395                 400

Ile Tyr Pro Gln Leu Arg Asp Phe Ile Arg Lys Tyr His Gln Ala Ser
                405                 410                 415

Ala Thr Arg


<210> SEQ ID NO 27
<211> LENGTH: 1260
<212> TYPE: DNA
<213> ORGANISM: Cupriavidus necator

<400> SEQUENCE: 27

atgctctacc aattgcatga gttccagcgc tcgatcctgc acccgctgac cgcgtgggcc      60

caggcgaccg ccaagacctt caccaacccc ctcagcccgc tctcgctggt tcccggcgca     120

ccccgcctgg ctgccggcta tgaactgctg taccggctcg gcaaggaata cgaaaagccg     180

gcattcgaca tcaagtcggt gcgctccaac gggcgcgaca tccccatcgt cgagcagacc     240
```

```
gtgcttgaaa agccgttctg caagctggtg cgcttcaagc gctatgccga cgacccggag    300
accatcaagc tgctcaagga tgagccggtg gtgctggtgg ccgcgccgct gtcgggccac    360
catgccacgc tgctgcgcga cacggtgcgc acgctgctgc aggaccacaa ggtctacgtc    420
accgactgga tcgacgcacg catggtgccg gtcgaggaag gcgcgttcca cctgtcggac    480
tacatctact acatccagga attcatccgc catatcggcg ccgagaacct gcatgtgatc    540
tcggtatgcc agcccaccgt gccggtgctg gccgcgatct cgctgatggc ctcggccggc    600
gagaagacgc cgcgcaccat gaccatgatg ggcggcccga tcgacgcccg caagagcccc    660
accgcggtca actcgctggc gaccaacaag tcgttcgagt ggttcgagaa caacgtcatc    720
tacaccgtgc cggccaacta ccccggccac ggccgccgcg tctacccggg ctttttgcag    780
catgccggtt tcgtggcgat gaacccggac cggcaccttt cctcgcacta tgacttctac    840
ctgagcctgg tcgagggcga tgcggatgac gccgaagccc acgtgcgctt ctacgacgaa    900
tacaacgcgg tgctcgacat ggccgccgag tactacctcg acaccatccg cgaggtgttc    960
caggaattcc gcctggccaa cggcacctgg gccatcgacg gcaatccggt gcggccgcag   1020
gacatcaaga gcaccgcgct gatgaccgtc gagggcgaac tggacgacat ctcgggcgcg   1080
ggccagaccg ccgcggcgca cgacctgtgc gccggcatcc cgaaaatccg caagcagcac   1140
ctgaacgcgg cacactgcgg ccactacggc atcttctcgg gccggcgctg gcgcgaagag   1200
atctacccgc agctgcgcga ctttatccgc aagtaccacc aggcctcggc caccaggtaa   1260
```

```
<210> SEQ ID NO 28
<211> LENGTH: 419
<212> TYPE: PRT
<213> ORGANISM: Cupriavidus necator

<400> SEQUENCE: 28

Met His Ile Ala Ala Arg Lys Asn Gln Asn Ser Gly Asp Arg Ala Met
1               5                   10                  15

Leu Tyr His Ala Tyr Gln Ile Tyr Ala Asp Met Ile Leu Pro Ala Cys
            20                  25                  30

Thr Leu Ala Glu Leu Ala Ala Ala Thr Leu Ala Ala Asn Pro Arg Ser
        35                  40                  45

Gly Gly Phe Asp Ala Val Pro Arg Leu Arg Ala Ala Cys Glu Leu Ile
    50                  55                  60

Ala Leu Val Arg Leu Thr His His Arg Pro Ala Phe Gly Ile Asp His
65                  70                  75                  80

Ala Thr Val Gly Gly Gln Pro Val Pro Val Thr Glu Glu Val Val Ala
                85                  90                  95

Arg Thr Pro Phe Cys Ser Leu Leu His Phe Arg Arg His Gly Ile Val
            100                 105                 110

Gly Gln Pro Arg Val Leu Leu Val Ala Pro Met Ser Gly His Phe Ala
        115                 120                 125

Thr Leu Leu Arg Gly Thr Val Gln Thr Met Leu Ala Asp His Asp Val
    130                 135                 140

Tyr Leu Thr Asp Trp His Asn Pro Arg Asp Ile Pro Leu Leu Ala Gly
145                 150                 155                 160

Arg Phe Gly Phe Asp Glu Phe Val Gln His Leu Ile Gly Phe Leu Gln
                165                 170                 175

Thr Leu Gly Gly Gly Thr His Leu Val Ala Ile Cys Gln Pro Ala Val
            180                 185                 190
```

-continued

```
Ala Ala Leu Ala Ala Ala Ala Leu Met Ala Glu Asp Gly Asp Pro Ala
        195                 200                 205

Gln Pro Pro Ser Leu Thr Leu Met Ala Gly Pro Ile Asp Ala Arg Val
    210                 215                 220

Asn Pro Thr Lys Val Asn Ala Leu Ala Met Ser Gln Pro Leu Glu Trp
225                 230                 235                 240

Phe Glu Arg Thr Leu Ile Gly Met Val Pro Leu Arg Phe Ala Gly Ala
                245                 250                 255

Met Arg Arg Val Tyr Pro Gly His Val Gln Leu Leu Ala Phe Met Ser
            260                 265                 270

Met Asn Pro Glu Arg His Glu Gln Ala Leu Arg Glu Leu Tyr Ala Leu
        275                 280                 285

Arg Glu Arg Gly Glu His Asp Lys Ala Asp Ala Ile Arg Asp Phe Tyr
    290                 295                 300

Ile Glu Tyr Phe Ala Thr Met Asp Leu Thr Ala Glu Phe Tyr Leu Glu
305                 310                 315                 320

Thr Val Ser Leu Val Phe Gln Arg Phe Leu Leu Ala Gln Gly Leu Leu
                325                 330                 335

Asp Val Ser Gly Arg Arg Val Arg Thr Arg Ala Ile His Arg Thr Ala
            340                 345                 350

Leu Leu Thr Val Glu Gly Glu Arg Asp Asp Ile Cys Ala Ile Gly Gln
        355                 360                 365

Thr Val Ala Ala Gln Asp Leu Cys Ser Ser Leu Arg Pro Tyr Met Arg
    370                 375                 380

Met His His Val Gln Thr Gly Val Gly His Tyr Gly Val Phe Asn Gly
385                 390                 395                 400

Arg Arg Trp Glu Thr Gln Val Tyr Pro Leu Val Arg Asn Thr Ile Tyr
                405                 410                 415

Thr Ser Ser


<210> SEQ ID NO 29
<211> LENGTH: 1260
<212> TYPE: DNA
<213> ORGANISM: Cupriavidus necator

<400> SEQUENCE: 29

atgcatattg cggctcgcaa gaaccagaat agcggggacc gagccatgct gtaccacgcc      60

taccagatct acgcggacat gatactgccg gcctgcacgc tggcggagct ggctgccgcg     120

acgctggcgg caaatcccag gtccggtggt ttcgacgcgg tgccccgcct gcgtgccgcc     180

tgcgagctca tcgcactggt gcggctcacg caccaccggc cggccttcgg catcgaccac     240

gcaaccgtcg gcggccagcc ggtgccggtc accgaggaag tcgtcgcgcg cacgccgttc     300

tgctcgctgc tgcacttccg ccgccacggc atcgtcggcc agccgcgcgt gctgctggtg     360

gcgccgatgt ccggccactt cgccacgctg ctgcgcggca cggtccagac catgctggcc     420

gaccacgacg tctatctcac cgactggcac aaccccccgcg acattccgtt gctggccggg     480

cgcttcggct tcgatgaatt cgtgcagcac ctgatcggct tcctgcagac gctgggcgga     540

ggcacgcatc tggtggcgat ttgccagcct gccgtggcag cgctggcggc agcggcactc     600

atggccgagg acggggatcc cgcccagccg cccagcctga cgctgatggc cggccccatc     660

gacgcgcgcg tcaatccgac caaggtcaac gcgctggcca tgagccaacc cctcgaatgg     720

ttcgagcgca ccttgatcgg catggtgccg ctgcgctttg ccggcgcgat gcggcgcgtc     780

tacccgggcc acgtgcagct gctggccttc atgagcatga acccggagcg gcacgaacag     840
```

gcgctgcgcg agctctacgc cctgcgcgag cgcggcgagc acgacaaggc cgatgccatc 900
cgcgacttct acatcgagta cttcgccacc atggacctga ccgcggagtt ctacctggaa 960
accgtcagcc tggtattcca gcgcttcctg ctggcccagg gcctgcttga cgtgagcgga 1020
cgccgtgtcc gcacgcgcgc catccaccgc accgccctgc tcaccgtgga gggtgaacgc 1080
gacgatatct gcgccatcgg ccagaccgtg gcggcgcagg acctgtgctc cagcctgcgc 1140
ccctacatgc gcatgcatca tgtgcagacc ggggtcgggc actatggcgt gttcaacggc 1200
aggcggtggg agacgcaggt gtacccgctg gtgcgcaaca ccatctacac cagcagctaa 1260

<210> SEQ ID NO 30
<211> LENGTH: 502
<212> TYPE: PRT
<213> ORGANISM: Escherichia coli

<400> SEQUENCE: 30

Met Thr Glu Lys Lys Tyr Ile Val Ala Leu Asp Gln Gly Thr Thr Ser
1 5 10 15

Ser Arg Ala Val Val Met Asp His Asp Ala Asn Ile Ile Ser Val Ser
20 25 30

Gln Arg Glu Phe Glu Gln Ile Tyr Pro Lys Pro Gly Trp Val Glu His
35 40 45

Asp Pro Met Glu Ile Trp Ala Thr Gln Ser Ser Thr Leu Val Glu Val
50 55 60

Leu Ala Lys Ala Asp Ile Ser Ser Asp Gln Ile Ala Ala Ile Gly Ile
65 70 75 80

Thr Asn Gln Arg Glu Thr Thr Ile Val Trp Glu Lys Glu Thr Gly Lys
85 90 95

Pro Ile Tyr Asn Ala Ile Val Trp Gln Cys Arg Arg Thr Ala Glu Ile
100 105 110

Cys Glu His Leu Lys Arg Asp Gly Leu Glu Asp Tyr Ile Arg Ser Asn
115 120 125

Thr Gly Leu Val Ile Asp Pro Tyr Phe Ser Gly Thr Lys Val Lys Trp
130 135 140

Ile Leu Asp His Val Glu Gly Ser Arg Glu Arg Ala Arg Arg Gly Glu
145 150 155 160

Leu Leu Phe Gly Thr Val Asp Thr Trp Leu Ile Trp Lys Met Thr Gln
165 170 175

Gly Arg Val His Val Thr Asp Tyr Thr Asn Ala Ser Arg Thr Met Leu
180 185 190

Phe Asn Ile His Thr Leu Asp Trp Asp Asp Lys Met Leu Glu Val Leu
195 200 205

Asp Ile Pro Arg Glu Met Leu Pro Glu Val Arg Arg Ser Ser Glu Val
210 215 220

Tyr Gly Gln Thr Asn Ile Gly Gly Lys Gly Gly Thr Arg Ile Pro Ile
225 230 235 240

Ser Gly Ile Ala Gly Asp Gln Gln Ala Ala Leu Phe Gly Gln Leu Cys
245 250 255

Val Lys Glu Gly Met Ala Lys Asn Thr Tyr Gly Thr Gly Cys Phe Met
260 265 270

Leu Met Asn Thr Gly Glu Lys Ala Val Lys Ser Glu Asn Gly Leu Leu
275 280 285

Thr Thr Ile Ala Cys Gly Pro Thr Gly Glu Val Asn Tyr Ala Leu Glu
290 295 300

-continued

```
Gly Ala Val Phe Met Ala Gly Ala Ser Ile Gln Trp Leu Arg Asp Glu
305                 310                 315                 320

Met Lys Leu Ile Asn Asp Ala Tyr Asp Ser Glu Tyr Phe Ala Thr Lys
                325                 330                 335

Val Gln Asn Thr Asn Gly Val Tyr Val Val Pro Ala Phe Thr Gly Leu
            340                 345                 350

Gly Ala Pro Tyr Trp Asp Pro Tyr Ala Arg Gly Ala Ile Phe Gly Leu
        355                 360                 365

Thr Arg Gly Val Asn Ala Asn His Ile Ile Arg Ala Thr Leu Glu Ser
    370                 375                 380

Ile Ala Tyr Gln Thr Arg Asp Val Leu Glu Ala Met Gln Ala Asp Ser
385                 390                 395                 400

Gly Ile Arg Leu His Ala Leu Arg Val Asp Gly Gly Ala Val Ala Asn
                405                 410                 415

Asn Phe Leu Met Gln Phe Gln Ser Asp Ile Leu Gly Thr Arg Val Glu
            420                 425                 430

Arg Pro Glu Val Arg Glu Val Thr Ala Leu Gly Ala Ala Tyr Leu Ala
        435                 440                 445

Gly Leu Ala Val Gly Phe Trp Gln Asn Leu Asp Glu Leu Gln Glu Lys
    450                 455                 460

Ala Val Ile Glu Arg Glu Phe Arg Pro Gly Ile Glu Thr Thr Glu Arg
465                 470                 475                 480

Asn Tyr Arg Tyr Ala Gly Trp Lys Lys Ala Val Lys Arg Ala Met Ala
                485                 490                 495

Trp Glu Glu His Asp Glu
            500
```

<210> SEQ ID NO 31
<211> LENGTH: 1509
<212> TYPE: DNA
<213> ORGANISM: Escherichia coli

<400> SEQUENCE: 31

```
atgactgaaa aaaaatatat cgttgcgctc gaccagggca ccaccagctc ccgcgcggtc     60

gtaatggatc acgatgccaa tatcattagc gtgtcgcagc gcgaatttga gcaaatctac    120

ccaaaaccag gttgggtaga acacgaccca atggaaatct gggccaccca aagctccacg    180

ctggtagaag tgctggcgaa agccgatatc agttccgatc aaattgcagc tatcggtatt    240

acgaaccagc gtgaaaccac tattgtctgg gaaaaagaaa ccggcaagcc tatctataac    300

gccattgtct ggcagtgccg tcgtaccgca gaaatctgcg agcatttaaa acgtgacggt    360

ttagaagatt atatccgcag caataccggt ctggtgattg acccgtactt ttctggcacc    420

aaagtgaagt ggatcctcga ccatgtggaa ggctctcgcg agcgtgcacg tcgtggtgaa    480

ttgctgtttg gtacggttga tacgtggctt atctggaaaa tgactcaggg ccgtgtccat    540

gtgaccgatt acaccaacgc ctctcgtacc atgttgttca acatccatac cctggactgg    600

gacgacaaaa tgctggaagt gctggatatt ccgcgcgaga tgctgccaga agtgcgtcgt    660

tcttccgaag tatacggtca gactaacatt ggcggcaaag gcggcacgcg tattccaatc    720

tccgggatcg ccggtgacca gcaggccgcg ctgtttggtc agttgtgcgt gaaagaaggg    780

atggcgaaga acacctatgg cactggctgc tttatgctga tgaacactgg cgagaaagcg    840

gtgaaatcag aaaacggcct gctgaccacc atcgcctgcg gcccgactgg cgaagtgaac    900

tatgcgttgg aaggtgcggt gtttatggca ggcgcatcca ttcagtggct gcgcgatgaa    960
```

-continued

```
atgaagttga ttaacgacgc ctacgattcc gaatatttcg ccaccaaagt gcaaaacacc   1020

aatggtgtgt atgtggttcc ggcatttacc gggctgggtg cgccgtactg ggacccgtat   1080

gcgcgcgggg cgattttcgg tctgactcgt ggggtgaacg ctaaccacat tatacgcgcg   1140

acgctggagt ctattgctta tcagacgcgt gacgtgctgg aagcgatgca ggccgactct   1200

ggtatccgtc tgcacgccct gcgcgtggat ggtggcgcag tagcaaacaa tttcctgatg   1260

cagttccagt ccgatattct cggcacccgc gttgagcgcc cggaagtgcg cgaagtcacc   1320

gcattgggtg cggcctatct cgcaggcctg gcggttggct tctggcagaa cctcgacgag   1380

ctgcaagaga aagcggtgat tgagcgcgag ttccgtccag gcatcgaaac cactgagcgt   1440

aattaccgtt acgcaggctg gaaaaaagcg gttaaacgcg cgatggcgtg ggaagaacac   1500

gacgaataa                                                            1509
```

```
<210> SEQ ID NO 32
<211> LENGTH: 523
<212> TYPE: PRT
<213> ORGANISM: Cupriavidus necator

<400> SEQUENCE: 32

Met Asn Gln Pro Ala Ala Gln Ala Gln Arg Pro Ala Ser Ser Gln Leu
1               5                   10                  15

Pro Thr Glu Pro Gln Tyr Val Leu Ala Leu Asp Gln Gly Thr Ser Ser
            20                  25                  30

Ser Arg Ala Ile Leu Phe Asp His Ala Gly Asn Val Val Arg Leu Ala
        35                  40                  45

Gln Arg Glu Phe Arg Gln Tyr Tyr Pro His Pro Gly His Val Glu His
    50                  55                  60

Asp Pro Tyr Glu Ile Trp Gln Ser Gln Leu Ala Val Ala His Ala Val
65                  70                  75                  80

Leu Ser Asp Ala Gly Ile Ser Ala Ala Gln Val Arg Ala Ile Gly Ile
                85                  90                  95

Thr Asn Gln Arg Glu Thr Thr Val Leu Trp Asp Arg Lys Thr Gly Glu
            100                 105                 110

Pro Val Gly Arg Ala Leu Val Trp Gln Asp Arg Arg Thr Ala Pro Met
        115                 120                 125

Cys Glu Ala Leu Gln Ala Ala Gly His Gly Glu Leu Phe Arg Asp Lys
    130                 135                 140

Thr Gly Leu Ile Ile Asp Ala Tyr Phe Ser Gly Thr Lys Leu Arg Trp
145                 150                 155                 160

Met Leu Asp Asn Ile Glu Gly Ala Arg Glu Arg Ala Gln Arg Gly Glu
                165                 170                 175

Leu Ala Phe Gly Thr Val Asp Ser Trp Leu Ile Trp Gln Leu Thr Asp
            180                 185                 190

Gly Ala Arg His Val Thr Asp Val Ser Asn Ala Ser Arg Thr Met Leu
        195                 200                 205

Phe Asn Ile His Asn Phe Glu Trp Asp Asp Ala Leu Leu Ala Leu Leu
    210                 215                 220

Asp Ile Pro His Ala Leu Leu Pro Glu Val Val Ala Ser Ser Gly Glu
225                 230                 235                 240

Val Ala Arg Thr Ser Ala Arg Leu Phe Gly Met Gln Ile Pro Ile Ala
                245                 250                 255

Gly Ile Ala Gly Asp Gln Gln Ala Ala Thr Phe Gly Gln Ala Cys Leu
            260                 265                 270
```

```
Ser Pro Gly Met Ala Lys Asn Thr Tyr Gly Thr Gly Cys Phe Leu Leu
        275                 280                 285

Met Asn Thr Gly Ser Gln Pro Val Thr Ser His Asn Arg Leu Leu Thr
    290                 295                 300

Thr Ile Gly Trp Gln Ile Arg Gly Gln Thr Gln Tyr Cys Leu Glu Gly
305                 310                 315                 320

Gly Val Phe Met Gly Gly Ala Thr Ile Gln Trp Leu Arg Asp Gly Leu
                325                 330                 335

Lys Ile Ile Asn Ser Ala Pro Glu Val Glu Pro Leu Ala Arg Gln Cys
            340                 345                 350

Asp Asp Thr Gly Gly Val Val Leu Val Pro Ala Phe Ala Gly Leu Gly
        355                 360                 365

Ala Pro His Trp Asp Pro Phe Ala Arg Gly Thr Leu Val Gly Met Thr
    370                 375                 380

Arg Gly Thr Gly Arg Pro Gln Ile Ala Arg Ala Ala Leu Glu Ser Ile
385                 390                 395                 400

Ala Leu Gln Ser Val Asp Val Leu Glu Ala Met Arg Lys Asp Ala Gly
                405                 410                 415

Ile Ser Leu Ala Glu Leu Arg Val Asp Gly Gly Ala Ser Arg Ser Asp
            420                 425                 430

Leu Leu Met Gln Met Gln Ala Asp Leu Leu Gly Thr Pro Val Val Arg
        435                 440                 445

Pro Arg Val Thr Glu Thr Thr Ala Leu Gly Ala Ala Tyr Leu Ala Gly
    450                 455                 460

Leu Ala Thr Gly Tyr Trp Ser Asp Pro Ala Glu Ile Ala Gln Gln Trp
465                 470                 475                 480

Gln Val Glu Arg Arg Phe Glu Pro Asn Leu Ser Ala Asp Ala Arg Gly
                485                 490                 495

His Arg Leu Ala Arg Trp His Arg Ala Val Asp Arg Ala Arg Asp Trp
            500                 505                 510

Ala Arg Glu Asp Glu Ala Ser Gly Ser His Ala
        515                 520
```

<210> SEQ ID NO 33
<211> LENGTH: 1572
<212> TYPE: DNA
<213> ORGANISM: Cupriavidus necator

<400> SEQUENCE: 33

```
atgaaccagc cagccgcgca ggcccagcgc cctgcatcgt cccagcttcc caccgagccg     60

caatatgtgc tggcgctcga ccagggcacc agcagctcgc gggccatcct gttcgaccat    120

gccggcaatg tggtgcggct cgcgcagcgc gagttccgcc aatattaccc acatcccggc    180

catgtcgagc acgaccccta cgagatctgg caatcgcagc tggcggtggc gcacgcggtg    240

ctgtccgatg ccggcatctc ggccgcgcag gtgcgcgcca tcggcatcac caaccagcgc    300

gagaccactg tgctgtggga ccgcaagacc ggcgagccgg tcgggcgcgc gctggtctgg    360

caggaccgcc gcaccgcgcc catgtgcgag gcgctgcagg ccgccggcca cggcgagctg    420

ttccgcgaca agaccggcct gatcatcgat gcctacttct ccggcaccaa gctgcgctgg    480

atgctcgaca acatcgaagg cgcgcgcgaa cgcgcccagc gcggcgagct ggccttcggc    540

accgtcgaca gctggctgat ctggcagttg accgacggcg cgcgccatgt caccgatgtg    600

tcaaatgcct cgcgcaccat gctgttcaat atccacaact tcgagtggga cgatgcgctg    660
```

-continued

```
ctggcgctgc tggacatccc gcacgcgctg ctgcccgagg tggtggcgtc cagcggcgag    720

gtggcgcgca cctcggcgcg gctgttcggc atgcagatcc ccattgccgg catcgccggc    780

gaccagcagg ccgccacctt cggccaggcc tgcctgtcgc cgggcatggc caagaacacc    840

tacggcaccg gctgcttcct gctgatgaat accggctcgc agccggtcac gtcgcacaac    900

cggctgctga ccacgatcgg ctggcagatc cgcggccaga cgcaatattg cctggaaggc    960

ggcgtgttca tgggcggcgc caccatccag tggctgcgcg acggcctcaa gatcatcaat   1020

agcgctcccg aggtcgagcc gctggcgcgc cagtgcgacg acaccggcgg cgtggtgctg   1080

gtgcccgcct ttgccggcct gggcgcgccg cactgggacc cgtttgcacg cggcacgctg   1140

gttggcatga cgcgcggcac cggccggccg cagatcgcgc gcgcggcgct ggaatcgatc   1200

gcgctgcaga gcgtcgacgt gctggaagcc atgcggaagg atgccggcat ctcgctggcc   1260

gaactgcgcg tggacggtgg cgcctcgcgc agcgacctgc tgatgcagat gcaggccgac   1320

ctgctcggca ccccggtggt ccgcccgcgc gtgaccgaaa ccaccgcgct gggcgccgcc   1380

tacctggcgg gactggccac cggttactgg agcgatccgg cggagatcgc gcagcaatgg   1440

caggtggagc ggcgctttga gccgaacctg tcggctgacg cgcgcggcca ccggctggcg   1500

cgctggcatc gcgcagtcga ccgcgcgcgc gactgggcgc gcgaggacga agccagcggc   1560

agccacgcct ga                                                        1572
```

<210> SEQ ID NO 34
<211> LENGTH: 507
<212> TYPE: PRT
<213> ORGANISM: Cupriavidus necator

<400> SEQUENCE: 34

```
Met Thr Gln Arg Arg Asn Val Ile Leu Ala Ile Asp Glu Gly Thr Ser
1               5                   10                  15

Gly Thr Arg Ala Ala Val Val Ala Ala Asp Gly His Val Met Cys Leu
            20                  25                  30

Glu Tyr Thr Thr Leu Glu Val Arg Ser Pro Cys Pro Gly Val Val Glu
        35                  40                  45

Gln Asp Ala Asp Val Leu Leu Asp Lys Thr Leu Ala Val Cys Arg Ala
    50                  55                  60

Thr Leu Ala Gln Ala Ala Arg Glu Asn Leu Thr Val Thr Ala Leu Ala
65                  70                  75                  80

Ile Ala Thr Gln Arg Ala Thr Ala Val Leu Trp Asp Thr Gln Thr Gly
                85                  90                  95

Arg Ala Leu Val Pro Ala Met Val Trp Gln Asp Thr Arg Tyr Ala Ala
            100                 105                 110

Asp Leu Asp Gln Leu Ala Pro Ala Trp Asp Ala Thr Leu Arg Glu Ala
        115                 120                 125

Val Gly Arg Pro Thr Gly Val Arg Ser Pro Tyr Leu Trp Ala Ala Arg
    130                 135                 140

His Leu Arg Asp Thr Pro Ala Val Ala Asp Ala Phe Arg Ala Arg Gln
145                 150                 155                 160

Leu Ala Phe Gly Thr Ile Asp Ser Trp Leu Leu Trp His Leu Ser Thr
                165                 170                 175

Ala Arg Thr Cys Ile Thr Thr Pro Thr Asn Ala Thr Ser Cys Asn Ala
            180                 185                 190

Tyr Val Leu Thr Gly His Arg Tyr Gln Leu Asp Trp Ile Asp Ala Leu
        195                 200                 205
```

-continued

```
Gly Phe Pro Arg Glu Leu Leu Pro Glu Leu Arg Gln Asp Ala Asp Asn
    210                 215                 220

Phe Gly Arg Thr Arg Pro Asp Val Leu Gly Ile Asp Val Pro Ile Leu
225                 230                 235                 240

Ala Cys Ala Gly Asp Gln Leu Ala Gly Ala Ile Gly Leu Gly Cys Leu
                245                 250                 255

Asp Ala Gly Gln Ala Met Cys Leu His Gly Thr Gly Ser Phe Val Asp
            260                 265                 270

Leu Val Val Gly Pro Asn Leu Pro Ala Arg Ser Gly Lys Ser Asp Ser
        275                 280                 285

Thr Leu Thr Met Thr Ala Arg Arg Gln Leu Gly Val Ser His Phe Ser
    290                 295                 300

Val Glu Thr Phe Val Ala Thr Thr Gly Ser Ala Leu Asn Trp Val Cys
305                 310                 315                 320

Asp Lys Leu Gly Trp Phe Glu Asn Ala Arg Gln Ile Ser Ala Leu Ala
                325                 330                 335

Ser Thr Val Ala Ser Ser Arg Gly Val Thr Phe Ile Pro Ala Leu Thr
            340                 345                 350

Gly Leu Arg Val Pro Arg Met Gln Pro Glu Ala Arg Ala Ala Leu Thr
        355                 360                 365

Gly Ile Ser Met Ala Thr Thr Gln Ala Glu Met Ala Phe Ala Ile Leu
    370                 375                 380

Glu Gly Ile Ala His Ser Val Thr Ser Cys Ile Glu Ala Asn Arg Glu
385                 390                 395                 400

Ile Ala Gly Val Pro Val Ser Glu Leu Val Val Gly Gly Gly Leu Ser
                405                 410                 415

Gly Ser Asp Ala Leu Leu Gln Met Gln Ala Asp Leu Ser Gly Ile Ser
            420                 425                 430

Ile His Arg Met Lys Glu Thr Asp Arg Ala Ser Leu Arg Gly Ile Ala
        435                 440                 445

Tyr Leu Ala Gly Ser Ser Gly Leu Leu Trp Asp Ser Met Gln Gln Ala
    450                 455                 460

Arg Thr Thr Thr Thr Pro Asp Ala Val Phe Glu Pro Ala Ile Ser Ala
465                 470                 475                 480

Asp Glu Arg Ala Gln Arg Arg Ala Leu Trp His Ala Arg Val Ala Ser
                485                 490                 495

Glu Leu Asn His Ala Asp Ala Leu Ala Val His
            500                 505
```

<210> SEQ ID NO 35
<211> LENGTH: 1524
<212> TYPE: DNA
<213> ORGANISM: Cupriavidus necator

<400> SEQUENCE: 35

```
atgacccagc gcagaaatgt catccttgcg atcgatgagg gcacctcagg cacccgggca      60

gcggtggtcg ccgctgacgg tcatgtcatg tgcctcgagt acaccacgct tgaggtccgt     120

tcgccctgcc ctggcgtggt cgagcaggac gccgacgtcc tgctcgacaa gaccctggca     180

gtttgccgcg ccaccctggc acaggctgcc cgcgaaaacc tgaccgtcac cgccctcgcc     240

atcgcgaccc agcgcgccac cgcggtactg tgggacacgc agaccggacg tgcgctggta     300

cccgccatgg tgtggcagga cacgcgatac gcagccgatc tggatcagct tgcgccggca     360

tgggacgcga ctctgcgcga agcagtcggc cgccccaccg gtgtgcgctc gccttaccta     420
```

-continued

```
tgggcggcgc ggcacctgcg cgacacgccg gctgtggctg acgccttccg tgcgcgccag    480

ctcgccttcg gcaccatcga cagctggctg ctttggcacc tgtcgacggc acgcacgtgc    540

atcaccacgc cgaccaacgc cacttcctgc aacgcctatg tactgaccgg gcatcgctac    600

cagctcgact ggatcgacgc gcttggcttt ccgcgcgagc tgctgcctga gctgcgccag    660

gatgcggaca acttcggccg cacgcggccg gacgtgctgg ggattgacgt gccgatcctg    720

gcttgtgccg ggaccagct cgccggcgca atcggcctgg gatgtctcga tgccggccag    780

gcgatgtgcc tgcatggcac cggcagcttc gtcgacctgg tagtcggtcc gaaccttcct    840

gcccgcagcg gcaagtcgga cagcaccctg accatgaccg cgcgccggca actgggcgtg    900

tcgcatttct ccgtcgaaac ctttgtcgcc accaccggct ccgcgctcaa ctgggtctgc    960

gacaagctcg gctggttcga gaacgccagg caaatcagtg cgctggccag caccgttgcg   1020

tcttcacgag gcgtgacctt tattcccgcg ctgaccggcc tgcgcgtccc acgcatgcag   1080

cccgaggcgc gcgccgcact gaccggcatc tcgatggcaa cgacgcaggc cgagatggcc   1140

tttgccatcc ttgaaggcat tgcgcattcg gtgacttcct gcatcgaggc caaccgggag   1200

atcgcgggcg tgccggtgtc ggagctcgtg gttggcggcg gcttgtccgg cagcgatgcg   1260

ctgctgcaga tgcaggcgga tctcagcgga atttccatcc accgcatgaa ggagaccgac   1320

cgcgccagcc tgcgcggcat cgcttacctt gccggctcgt ccggcctgct ttgggattcc   1380

atgcagcagg cccggaccac caccaccccg gacgcagtat tcgaaccggc gatcagcgcc   1440

gatgagcgcg cccagcggcg cgcgctctgg catgcgcggg tggcatccga gctcaaccat   1500

gcggacgcgc ttgcggtcca ttaa                                          1524
```

<210> SEQ ID NO 36
<211> LENGTH: 241
<212> TYPE: PRT
<213> ORGANISM: Cupriavidus necator

<400> SEQUENCE: 36

```
Met Ser Thr Leu Ala Arg Arg Leu Val Ala Glu Gly Leu Gly Thr Ala
1               5                   10                  15

Leu Leu Val Ala Ile Val Val Gly Ser Gly Ile Arg Ala Glu Arg Leu
            20                  25                  30

Ala Ala Gly Asp Thr Ala Leu Ala Leu Leu Ala Asn Ser Leu Ala Thr
        35                  40                  45

Gly Ala Gly Leu Val Ala Leu Leu Val Ser Leu Gly Pro Val Ser Gly
    50                  55                  60

Gly His Phe Asn Pro Val Val Ser Leu Ser Ala Leu Leu Gln Gly Thr
65                  70                  75                  80

Leu Pro Pro Arg Asp Ala Leu Arg Tyr Val Leu Val Gln Val Ala Gly
                85                  90                  95

Gly Val Cys Gly Val Leu Ala Ala His Ala Met Phe Gly Glu Pro Ala
            100                 105                 110

Leu Ala Trp Ser Ala Gln Ser Arg Thr Gly Ala Ala Met Trp Trp Ser
        115                 120                 125

Glu Cys Val Ala Thr Phe Gly Leu Val Gly Val Gly Ile Gly Thr Leu
    130                 135                 140

Arg Ser Arg Pro Gln Leu Val Pro Phe Val Val Ala Gly Tyr Ile Ile
145                 150                 155                 160

Ala Gly Tyr Trp Phe Thr Ser Ser Thr Ser Phe Ala Asn Pro Ala Leu
                165                 170                 175
```

-continued

```
Thr Ile Ala Cys Ala Leu Thr Asp Thr Phe Thr Gly Ile Arg Pro Gln
            180                 185                 190

Asp Val Pro Gly Phe Val Leu Ala Gln Ile Gly Gly Gly Leu Ala Ala
        195                 200                 205

Thr Leu Leu Phe His Trp Leu Cys Arg Lys Pro Ala Ala Ala Ala Thr
    210                 215                 220

Ala Gln Ala Asp Trp Arg Ala Ala Pro Ala Ser Ala Pro Thr Ser Ala
225                 230                 235                 240

Asp
```

<210> SEQ ID NO 37
<211> LENGTH: 726
<212> TYPE: DNA
<213> ORGANISM: Cupriavidus necator

<400> SEQUENCE: 37

```
atgagtacgc tcgcacgccg cctggtggcc gaaggcctgg gcacggccct gctggtggcg      60

atcgtggtgg gctccggcat ccgtgccgag cgcctcgccg caggcgacac cgcgctggcg     120

ctgctggcca attcgctggc caccggggct gggctggtgg cgctgctggt gtcgctgggc     180

ccggtgtcgg gcggccattt caatccggtg gtgagcctgt cggcgctgct gcagggcacg     240

ctgccgccgc gcgatgcgct gcgctatgtg ctggtgcagg tggcgggcgg agtctgcggc     300

gtgctggccg cccatgcgat gttcggcgag ccggcgctgg cctggtcggc gcagagccgc     360

accggcgcgg cgatgtggtg gagcgagtgc gtggccacct tcggcctggt cggcgtgggc     420

atcggcacgc tgcgcagccg gccgcagctg gtgccgttcg tggtggcagg ctatatcatc     480

gcgggctact ggttcacgtc gtcgacctcg tttgccaacc cggcgctgac catcgcctgc     540

gcgctgaccg ataccttcac cgggatccgg ccgcaagacg tgccgggctt cgtgctggcc     600

cagatcggcg gcgggctggc tgccacgctg ctgttccact ggctgtgccg caaacccgct     660

gcggccgcca cggcgcaggc cgactggcgc gctgcgcccg ccagcgcccc taccagcgcc     720

gattga                                                                726
```

<210> SEQ ID NO 38
<211> LENGTH: 281
<212> TYPE: PRT
<213> ORGANISM: Escherichia coli

<400> SEQUENCE: 38

```
Met Ser Gln Thr Ser Thr Leu Lys Gly Gln Cys Ile Ala Glu Phe Leu
1               5                   10                  15

Gly Thr Gly Leu Leu Ile Phe Phe Gly Val Gly Cys Val Ala Ala Leu
            20                  25                  30

Lys Val Ala Gly Ala Ser Phe Gly Gln Trp Glu Ile Ser Val Ile Trp
        35                  40                  45

Gly Leu Gly Val Ala Met Ala Ile Tyr Leu Thr Ala Gly Val Ser Gly
    50                  55                  60

Ala His Leu Asn Pro Ala Val Thr Ile Ala Leu Trp Leu Phe Ala Cys
65                  70                  75                  80

Phe Asp Lys Arg Lys Val Ile Pro Phe Ile Val Ser Gln Val Ala Gly
                85                  90                  95

Ala Phe Cys Ala Ala Ala Leu Val Tyr Gly Leu Tyr Tyr Asn Leu Phe
            100                 105                 110

Phe Asp Phe Glu Gln Thr His His Ile Val Arg Gly Ser Val Glu Ser
        115                 120                 125
```

-continued

Val Asp Leu Ala Gly Thr Phe Ser Thr Tyr Pro Asn Pro His Ile Asn
    130                 135                 140

Phe Val Gln Ala Phe Ala Val Glu Met Val Ile Thr Ala Ile Leu Met
145                 150                 155                 160

Gly Leu Ile Leu Ala Leu Thr Asp Asp Gly Asn Gly Val Pro Arg Gly
                165                 170                 175

Pro Leu Ala Pro Leu Leu Ile Gly Leu Leu Ile Ala Val Ile Gly Ala
            180                 185                 190

Ser Met Gly Pro Leu Thr Gly Phe Ala Met Asn Pro Ala Arg Asp Phe
        195                 200                 205

Gly Pro Lys Val Phe Ala Trp Leu Ala Gly Trp Gly Asn Val Ala Phe
    210                 215                 220

Thr Gly Gly Arg Asp Ile Pro Tyr Phe Leu Val Pro Leu Phe Gly Pro
225                 230                 235                 240

Ile Val Gly Ala Ile Val Gly Ala Phe Ala Tyr Arg Lys Leu Ile Gly
                245                 250                 255

Arg His Leu Pro Cys Asp Ile Cys Val Val Glu Glu Lys Glu Thr Thr
            260                 265                 270

Thr Pro Ser Glu Gln Lys Ala Ser Leu
        275                 280

<210> SEQ ID NO 39
<211> LENGTH: 846
<212> TYPE: DNA
<213> ORGANISM: Escherichia coli

<400> SEQUENCE: 39
atgagtcaaa catcaacctt gaaaggccag tgcattgctg aattcctcgg taccgggttg 60
ttgattttct tcggtgtggg ttgcgttgca gcactaaaag tcgctggtgc gtcttttggt 120
cagtgggaaa tcagtgtcat ttggggactg gggggtggcaa tggccatcta cctgaccgca 180
ggggtttccg gcgcgcatct taatcccgct gttaccattg cattgtggct gtttgcctgt 240
ttcgacaagc gcaaagttat tccttttatc gtttcacaag ttgccggcgc tttctgtgct 300
gcggctttag tttacgggct ttactacaat ttatttttcg acttcgagca gactcatcac 360
attgttcgcg gcagcgttga aagtgttgat ctggctggca ctttctctac ttaccctaat 420
cctcatatca attttgtgca ggctttcgca gttgagatgg tgattaccgc tattctgatg 480
gggctgatcc tggcgttaac ggacgatggc aacggtgtac cacgcggccc tttggctccc 540
ttgctgattg gtctactgat tgcggtcatt ggcgcatcta tgggcccatt gacaggtttt 600
gccatgaacc cagcgcgtga cttcggtccg aaagtctttg cctggctggc gggctggggc 660
aatgtcgcct ttaccggcgg cagagacatt ccttacttcc tggtgccgct tttcggccct 720
atcgttggcg cgattgtagg tgcatttgcc taccgcaaac tgattggtcg ccatttgcct 780
tgcgatatct gtgttgtgga agaaaaggaa accacaactc cttcagaaca aaaagcttcg 840
ctgtaa 846

<210> SEQ ID NO 40
<211> LENGTH: 36
<212> TYPE: DNA
<213> ORGANISM: Artificial Sequence
<220> FEATURE:
<223> OTHER INFORMATION: primer

<400> SEQUENCE: 40

-continued aaagaagggc caattggcgc aacgcaatta atgtga 36

<210> SEQ ID NO 41
<211> LENGTH: 40
<212> TYPE: DNA
<213> ORGANISM: Artificial Sequence
<220> FEATURE:
<223> OTHER INFORMATION: primer

<400> SEQUENCE: 41
aacatacgag ccggaagcat aagtgtaaag cctggggtgc 40

<210> SEQ ID NO 42
<211> LENGTH: 40
<212> TYPE: DNA
<213> ORGANISM: Artificial Sequence
<220> FEATURE:
<223> OTHER INFORMATION: primer

<400> SEQUENCE: 42
gcaccccagg ctttacactt atgcttccgg ctcgtatgtt 40

<210> SEQ ID NO 43
<211> LENGTH: 46
<212> TYPE: DNA
<213> ORGANISM: Artificial Sequence
<220> FEATURE:
<223> OTHER INFORMATION: primer

<400> SEQUENCE: 43
tgattgtctc tctgcacgtg caattgtttc ctgtgtgaaa ttgtta 46

<210> SEQ ID NO 44
<211> LENGTH: 44
<212> TYPE: DNA
<213> ORGANISM: Artificial Sequence
<220> FEATURE:
<223> OTHER INFORMATION: primer

<400> SEQUENCE: 44
cacgtgcaga gagacaatca aatcatgact gaaaaaaaat atat 44

<210> SEQ ID NO 45
<211> LENGTH: 74
<212> TYPE: DNA
<213> ORGANISM: Artificial Sequence
<220> FEATURE:
<223> OTHER INFORMATION: primer

<400> SEQUENCE: 45
gctcggatcc actagtcggc tgccgactgg ttgaaccagg ccggcaggtc aggcttattc 60
gtcgtgttct tccc 74

<210> SEQ ID NO 46
<211> LENGTH: 32
<212> TYPE: DNA
<213> ORGANISM: Artificial Sequence
<220> FEATURE:
<223> OTHER INFORMATION: primer

<400> SEQUENCE: 46
gcgcatttaa atccggacct tcgtgcggct ca 32

<210> SEQ ID NO 47
<211> LENGTH: 43

-continued

<212> TYPE: DNA
<213> ORGANISM: Artificial Sequence
<220> FEATURE:
<223> OTHER INFORMATION: primer

<400> SEQUENCE: 47
actagtatcg atcaattgga ggactcctga tcgtgtgacg cga 43

<210> SEQ ID NO 48
<211> LENGTH: 42
<212> TYPE: DNA
<213> ORGANISM: Artificial Sequence
<220> FEATURE:
<223> OTHER INFORMATION: primer

<400> SEQUENCE: 48
caattgatcg atactagtag tcgggcagca ccaatgcgca tc 42

<210> SEQ ID NO 49
<211> LENGTH: 32
<212> TYPE: DNA
<213> ORGANISM: Artificial Sequence
<220> FEATURE:
<223> OTHER INFORMATION: primer

<400> SEQUENCE: 49
gcgcatttaa atcgccacgc tgtgcctgac ga 32

<210> SEQ ID NO 50
<211> LENGTH: 18
<212> TYPE: DNA
<213> ORGANISM: Artificial Sequence
<220> FEATURE:
<223> OTHER INFORMATION: Artificial linker sequence

<400> SEQUENCE: 50
caattgatcg atactagt 18

<210> SEQ ID NO 51
<211> LENGTH: 32
<212> TYPE: DNA
<213> ORGANISM: Artificial Sequence
<220> FEATURE:
<223> OTHER INFORMATION: primer

<400> SEQUENCE: 51
gcgcgcgaat tcgcgcaacg caattaatgt ga 32

<210> SEQ ID NO 52
<211> LENGTH: 34
<212> TYPE: DNA
<213> ORGANISM: Artificial Sequence
<220> FEATURE:
<223> OTHER INFORMATION: primer

<400> SEQUENCE: 52
gcgcgcattt aaataacagt tcgtcacgcc agcc 34

<210> SEQ ID NO 53
<211> LENGTH: 20
<212> TYPE: DNA
<213> ORGANISM: Artificial Sequence
<220> FEATURE:
<223> OTHER INFORMATION: primer

<400> SEQUENCE: 53
gcgttcaatc ctgacaatga 20

<210> SEQ ID NO 54
<211> LENGTH: 20
<212> TYPE: DNA
<213> ORGANISM: Artificial Sequence
<220> FEATURE:
<223> OTHER INFORMATION: primer

<400> SEQUENCE: 54
atgaaccagc cagccgcgca 20

<210> SEQ ID NO 55
<211> LENGTH: 34
<212> TYPE: DNA
<213> ORGANISM: Artificial Sequence
<220> FEATURE:
<223> OTHER INFORMATION: primer

<400> SEQUENCE: 55
gggcccattt aaattcttgt cgcggaacag ctcg 34

<210> SEQ ID NO 56
<211> LENGTH: 40
<212> TYPE: DNA
<213> ORGANISM: Artificial Sequence
<220> FEATURE:
<223> OTHER INFORMATION: primer

<400> SEQUENCE: 56
tcattgtcag gattgaacgc gcgcaacgca attaatgtga 40

<210> SEQ ID NO 57
<211> LENGTH: 42
<212> TYPE: DNA
<213> ORGANISM: Artificial Sequence
<220> FEATURE:
<223> OTHER INFORMATION: primer

<400> SEQUENCE: 57
tccgctcaca attccacaca ttatacgagc cggaagcata aa 42

<210> SEQ ID NO 58
<211> LENGTH: 42
<212> TYPE: DNA
<213> ORGANISM: Artificial Sequence
<220> FEATURE:
<223> OTHER INFORMATION: primer

<400> SEQUENCE: 58
tttatgcttc cggctcgtat aatgtgtgga attgtgagcg ga 42

<210> SEQ ID NO 59
<211> LENGTH: 40
<212> TYPE: DNA
<213> ORGANISM: Artificial Sequence
<220> FEATURE:
<223> OTHER INFORMATION: primer

<400> SEQUENCE: 59
tgcgcggctg gctggttcat gatttgattg tctctctgca 40

<210> SEQ ID NO 60
<211> LENGTH: 44
<212> TYPE: DNA
<213> ORGANISM: Artificial Sequence -continued

```
<220> FEATURE:
<223> OTHER INFORMATION: primer

<400> SEQUENCE: 60

cacgtgcaga gagacaatca aatcatgaac cagccagccg cgca                  44


<210> SEQ ID NO 61
<211> LENGTH: 74
<212> TYPE: DNA
<213> ORGANISM: Artificial Sequence
<220> FEATURE:
<223> OTHER INFORMATION: primer

<400> SEQUENCE: 61

gctcggatcc actagtcggc tgccgactgg ttgaaccagg ccggcaggtc aggctcaggc  60

gtggctgccg ctgg                                                    74
```